United States Patent
Erdelmeier et al.

(10) Patent No.: US 9,926,300 B2
(45) Date of Patent: Mar. 27, 2018

(54) 5-ACYLSULFANYL-HISTIDINE COMPOUNDS AS PRECURSORS OF THE CORRESPONDING 5-SULFANYLHISTIDINES AND THEIR DISULFIDES

(71) Applicant: TETRAHEDRON, Paris (FR)

(72) Inventors: Irene Erdelmeier, Paris (FR); Sylvain Daunay, Paris (FR)

(73) Assignee: TETRAHEDRON, Paris (FR)

( * ) Notice: Subject to any disclaimer, the term of this patent is extended or adjusted under 35 U.S.C. 154(b) by 0 days.

(21) Appl. No.: 15/314,628

(22) PCT Filed: May 29, 2015

(86) PCT No.: PCT/FR2015/051416
§ 371 (c)(1),
(2) Date: Nov. 29, 2016

(87) PCT Pub. No.: WO2015/181507
PCT Pub. Date: Dec. 3, 2015

(65) Prior Publication Data
US 2017/0190691 A1    Jul. 6, 2017

(30) Foreign Application Priority Data
May 30, 2014   (FR) ..................................... 14 54935

(51) Int. Cl.
*C07D 233/84*   (2006.01)
*C07D 403/12*   (2006.01)

(52) U.S. Cl.
CPC ......... *C07D 403/12* (2013.01); *C07D 233/84* (2013.01)

(58) Field of Classification Search
CPC .................................................. C07D 233/84
See application file for complete search history.

(56) References Cited

U.S. PATENT DOCUMENTS

| | | |
|---|---|---|
| 2012/0136159 A1 | 5/2012 | Erdelmeier et al. |
| 2012/0330029 A1 | 12/2012 | Erdelmeier et al. |

OTHER PUBLICATIONS

Holler et al., Journal of Organic Chemistry, 1987, 52, pp. 4420-4421.*
Reinhold et al., "Synthesis of a-N-Methylated Histidines", Department of Biochemistry, vol. 11, p. 258-260, Jul. 5, 1967.
Pathirana et al., "Imbricatine, an . . . Dermasterias imbricate", J. Am. Chem. Soc. 1986, 108, 8288-8289.
Vogt et al., "The biosynthesis . . . lyase reaction", Eur. J. Biochem., 268, 5229-5241 (2001).
Bailly et al., "Design, Synthesis . . . Ovothiol-Derived Diselenides", Bioorganic & Medicinal Chemistry 11 (2003), 4623-4630.
Ohba et al., Synthetic Studies . . . Synthesis of Tri-O-methylimbricatine, Tetrahedron 56 (1999) 4999-5016.
Liu et al., "Discovery of . . . Amide Hydrolase", ACS Medicinal Chemistry Letters, 2013, 4, 509-513.
Braunshausen et al., "Identification and . . . Biosynthetic Enzyme", Journal of the American Chemical Society, 2011, 133, 1757-1759.
Ito et al., "Structures of . . . Octopus vulgaris", JCSCC, 1976, 1042-1043.
Mashabela et al., "Substrate specificity . . . ovothiol biosynthesis", The Royal Society of Chemistry, 2013, 49, 7714-7716.
Palumbo et al., "Isolation and . . . Urchin Eggs", Tetrahedron Letters, vol. 23, No. 31, pp. 3207-3208, 1982.
Song et al., "Regioselectivity of the . . . Ovothiol Biosyntheses", Organic Letters, 2013, vol. 15, No. 18, 4854-4857.
Spaltenstein et al., "A New Synthesis of 4- and 5-Imidazolethiols", J. Org. Chem. 1987, 52, 2977-2979.
Turner et al., "Ovothiol: A Novel . . . Activity on Ovoperoxidase", The Journal of Biological Chemistry, vol. 261, No. 28, pp. 13056-13063, 1986.
Hand et al., "Biological Chemistry of . . . Marine Origin", J. Nat. Prod. 2005, 68, 293-308.
Carroll et al., "Leptoclinidamines A-C, . . . Leptoclinides duras", J. Nat. Prod. 2009, 72, 696-699.
Phil De Luna et al., "A Density Functional . . . Ovothiol to Copper", The Journal of Physical Chemistry A, Apr. 16, 2013, pp. 1-29.
Holler et al., "Synthesis and . . . L-Ovothiols A and C", J. Org. Chem. 1987, 52, 4420-4421.
Ito et al., "Novel Reaction of . . . and Cystein-S-yldopas", JCS Chem. Comm. 1977, 251-252.
Piez et al., "Desalting of . . . Ion Exchange", Department of Chemistry, Northwestern University Dental School, 1952, pp. 669-672.
Rossi et al., "5-Thiolhistidine, A . . . of *Octopus vulgaris*", Comp. Biochem. Physiol. vol. 80B, No. 4, pp. 843-845, 1985.

* cited by examiner

*Primary Examiner* — Laura L. Stockton
(74) *Attorney, Agent, or Firm* — Clark & Brody

(57) ABSTRACT

The invention relates to a compound of the 5-acylsulfanyl-histidine type and the derivatives thereof, of general formula (I), wherein R1 to R3=H, alkyl, especially CH3; R4=H, alkyl, especially CH3, alkyle(C=O), substituted alkyl (C=O), aryl (C=O); β-alanyl (H2NCH2CH2 (C=O); α-amino-acyl; R5=alkyl, especially methyl, phenyl. The invention also relates to the use of said compound for producing compounds of the 5-sulfanyl-histidine type and the derivatives thereof, in addition to corresponding disulfides; and to the various methods for the production thereof.

14 Claims, 4 Drawing Sheets

Figure 1: Scheme for the synthesis of novel 5-acylsulfanyl-histidines compounds as precursors of the corresponding 5-sulfanylhistidines and their disulfides
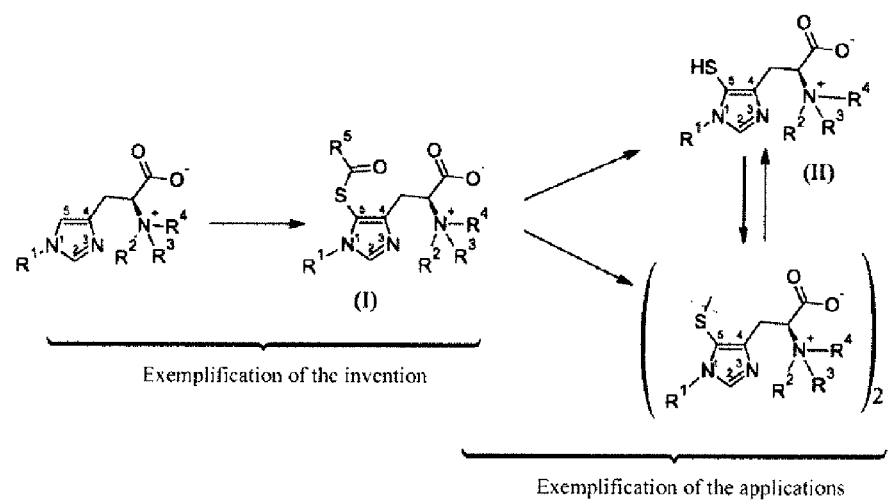

Figure 2: Representative spectrum ($^1$H NMR, 400 MHz) of the reaction mixture obtained in Example 1, preparation of L-5-acetylsulfanyl-histidine (Compound 1)
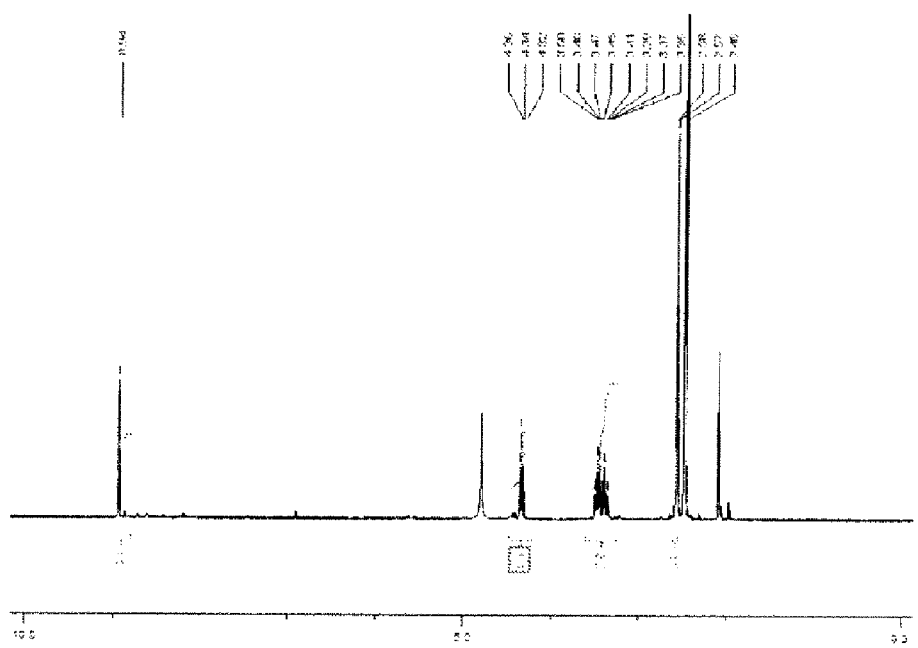

Figure 3: Representative spectrum (¹H NMR, 400 MHz) of the reaction mixture obtained in Example 3, preparation of L-5-acetylsulfanyl-α,N,N-dimethylhistidine (Compound 2)
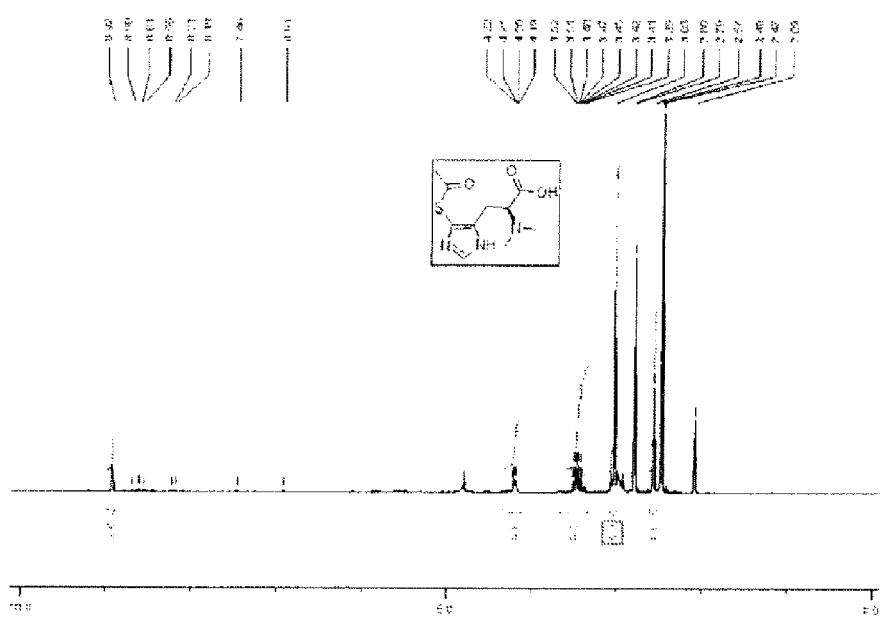

Figure 4: Representative spectrum ($^1$H NMR, 400 MHz) of the reaction mixture obtained in Example 5, preparation of L-5-acetylsulfanyl-α,N,N,N-trimethylhistidine (Compound 3)
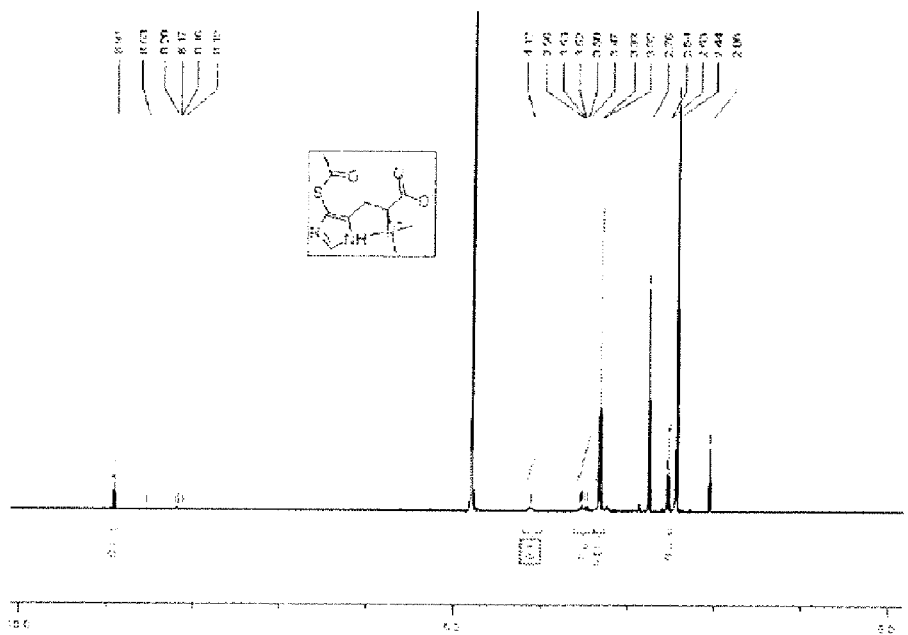

# 5-ACYLSULFANYL-HISTIDINE COMPOUNDS AS PRECURSORS OF THE CORRESPONDING 5-SULFANYLHISTIDINES AND THEIR DISULFIDES

The present invention relates to:
novel 5-acylsulfanyl-histidine compounds (and their derivatives);
methods for preparing same;
use thereof as precursors of the corresponding 5-sulfanylhistidines and their disulfides.

The present invention relates to novel 5-acylsulfanyl-histidine compounds and their derivatives, as well as to methods for preparing same and to the use thereof as precursors of the corresponding 5-sulfanylhistidines and their disulfides. More particularly, this invention relates to the synthesis of novel 5-acylsulfanyl-histidine compounds and their derivatives, their salts as direct precursors of the corresponding 5-sulfanylhistidines and their disulfides. The recent IUPAC nomenclature "sulfanyl" for the "—SH" group is used for the compounds described in the invention instead of the different terms used in the past in the literature, such as "thiohistidine," "thiolhistidine" or "mercaptohistidine."

PRIOR ART

The 5-sulfanyl-imidazole group is rarely found in nature (Caroll A. and Avrey V. M.; J. Nat. Prod.; 2009; 72; 696-699). Very few natural products comprising a 5-sulfanylhistidine backbone (methylated or not in position 3 of the imidazole ring) have been found to date (Hand C. E. and Honek J. F.; J. Nat. Prod.; 2005; 68; 293-308). Most are of bacterial or marine origin. A first example consists of the group of the adenochromines A, B and C (Ito S. and Prota G.; JCS Chem. Comm.; 1977; 251-252; Rossi F., Nardi G., Palumbo A. and Prota G.; Comp. Biochem. Physiol. 1985, 80b, 843-845) and the seco-adenochromines A, B and C (Ito S., Nardi G. and Prota G.; JCS Chem. Comm.; 1976; 1042). Imbricatine, produced by Dermasterias imbricate, constitutes a second example (Pathirana C. and Andersen R. J.; J. Am. Chem. Soc.; 1986; 108, 8288-8289). The ovothiols A, B and C. (Turner E., Klevit R. E. and Shapiro B. M.; J. Biol. Chem.; 1986; 261; 13056) constitute a third example of the even more restricted group of natural products comprising a 5-sulfanylhistidine backbone methylated in position 3 (It should be noted that the position of the methyl group was initially incorrectly located on the N1 nitrogen of histidine, as demonstrated in Holler et al. *JOC* 1987, 4421-4423 vs. Palumba et al., *THL* 1982, 3207-3208). Very recently, a new indole alkaloid containing a 5-sulfanylhistidine backbone, leptoclinidamine C, was found (Caroll A. and Avrey V. M.; J. Nat. Prod.; 2009; 72; 696-699).

The biosynthesis of the ovothiols A, B and C has been described (Vogt R. N., Spies H. S. C. and Steenkamp D. J.; Eur. J. Biochem.; 2001, 268, 5229-5241). The introduction of sulfur, in position 5 of the imidazole ring of L-histidine, is carried out in the presence of the sulfoxide synthase enzyme (OvoA) as well as of ferrous iron ($Fe^{2+}$) and oxygen 02. L-cysteine is used as sulfur donor leading to a sulfoxide intermediate (Braunshausen A. and Seebeck F.; JACS; 2011; 133, 1757). The latter is then transformed into ovothiol A, B or C in the presence of the sulfoxide lyase enzyme and pyridoxal phosphate, its cofactor (Mashabela G. and Seebeck F.; JCS Chem. Comm.; 2013, 7714-7716).

The preparation of 2-sulfanylhistidine and their derivatives by chemical synthesis has already been documented by the applicant (patent U.S. Ser. No. 13/121,891 and patent U.S. Ser. No. 13/500,887 A1).

The preparation of 5-sulfanylhistidine and of their derivatives by chemical synthesis turned out to be much more difficult than that of their 2-sulfanylhistidine isomers. Several synthesis strategies were considered and tested without success. To date, only 2 access routes have led only to the series of the 5-sulfanyl-3-methylhistidines. The first approach consisted of the de novo synthesis of the 5-sulfanylimidazole ring (Hopkins P. et al.; JOC; 1987, 52, 2977 and 4420) in the context of the synthesis of the ovothiols A and C in 10 to 12 steps. The second approach consisted of a nucleophilic substitution of a 5-bromoimidazole ring activated by a CHO carboxaldehyde electron-withdrawing group (Ohba M., Nishimura Y., Kato M. and Fujii T.; Tetrahedron; 1999, 55, 4999-5016) in the context of the synthesis of imbricatine. Currently, there is no known non-enzymatic chemical method for directly introducing a sulfur atom into the histidine or one of its derivatives in position 5 of the imidazole ring.

The article by SPALTENSTEIN in "The Journal of Organic Chemistry, Vol. 52, No. 14, pp. 2977-2979 discloses a method for preparing a compound 8 (p. 2978) obtained by the cyclization of the corresponding thionoamide, but the latter cannot correspond to any compound of the invention in view of the technical elements that follow.

In the same way, the article by Heng Song in Organic Letters, Vol. 15, No. 18, Sep. 20, 2013, pp. 4854-4857, entitled "Regioselectivity of the oxidative C—S Bond Formation in Ergothioneine and Ovothiol Biosyntheses," discloses a compound ovothiol (8) (p. 4855, scheme 1) which does not correspond to any compound of the invention in view of the technical elements that follow.

Indeed, as mentioned above, page 2, lines 2-5, the initial structure of the ovothiols A, B and C was defined incorrectly in these two articles by SPALTENSTEIN and Song with regard to the positioning of the methyl group on the nitrogen of the imidazole ring of histidine. Initially located incorrectly on the N1 nitrogen of histidine, this methyl group was "repositioned" on the N3 nitrogen, as demonstrated in Holler et al. JOC 1987, 20, 4421-4423 vs. Palumba et al., THL 1982, 3207-3208).

Thus, the structure of the ovothiols A, B and C is well established following the publication by Holler et al. (JOC 1987, 20, 4421-4423), already cited in the application and accepted by the scientific community according to the following examples:

Ovothiol C: see Bailly et al., Bioorg. Med. Chem., 2003, 11, 4623-4630, FIG. 1, p. 4624;
Ovothiols A, B and C: see De Luna et al., J. Phys. Chemistry, 2013, DOI: 10.1021/jp402514w;
Ovothiol A: see Mashabela et al., Chem. Comm., 2013, 49, 7714-7716.

Since the SPALTENSTEIN and Song documents are based on the erroneous location of the methyl in position N1, when it should be correctly located in position N3, the result is that the compound 8 of SPALTENSTEIN or Song (with the corrected structure) corresponds to the condition of formula (II) of the invention described below.

The 5-acylsulfanyl-histidine compounds and their derivatives would constitute very good precursors of 5-sulfanylhistidine and their derivatives. Since these 5-acylsulfanyl-histidine compounds and their derivatives are not known, it would therefore be necessary to have a synthesis method that makes it possible to directly introduce an acylsulfanyl group in position 5 of a histidine. To our knowledge, no such method has been described to date. This novel method for the direct introduction of an acylsulfanyl group in position 5 of histidine or of one of its derivatives would be all the more advantageous since it could be carried out without protective group and in water as a reaction solvent.

OBJECTS OF THE INVENTION

One of the objects of the present invention is thus to provide novel 5-acylsulfanyl-histidine compounds and their derivatives that are capable of being precursors of the corresponding 5-sulfanylhistidines and their disulfides.

Another object of the present invention is a method for preparing these novel 5-acylsulfanyl-histidine compounds and their derivatives using a novel method of direct introduction of an acylsulfanyl group in position 5 of a histidine or one of its derivatives without protective group and in water as solvent.

Another object of the present invention is the use of these novel 5-acylsulfanyl-histidine compounds and their derivatives as precursors of the corresponding 5-sulfanylhistidines and their disulfides.

These objects are achieved by the present invention which is based on the design and the preparation of novel 5-acylsulfanyl-histidine compounds and their derivatives, which are shown to be excellent precursors of the corresponding 5-sulfanylhistidines and their disulfides, by using a novel method for introducing an acylsulfanyl group. This has been exemplified by the applicant.

DESCRIPTION OF THE INVENTION

Thus, the object of the present invention is:

1) to solve the technical problem consisting in providing novel 5-acylsulfanyl-histidine compounds and their derivatives, thus constituting precursors of the corresponding 5-sulfanylhistidines and their disulfides;

2) to solve this technical problem according to a solution that includes a method for preparing these novel 5-acylsulfanyl-histidine derivatives using a novel method for directly introducing an acylsulfanyl group in position 5 of the imidazole ring of a histidine without protective group and in water as reaction solvent.

The technical problems stated above are solved for the first time simultaneously by the present invention, in a very easy and economic manner, the method for preparing said novel 5-acylsulfanyl-histidine derivatives being very simple to carry out while producing good yields.

According to a first aspect, the present invention relates to novel 5-acylsulfanyl-histidine compounds and their derivatives having the following general formula (I):

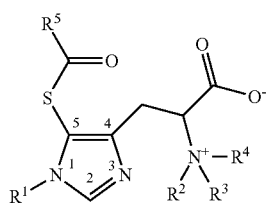

Where:
$R^1$=H, alkyl, in particular $CH_3$;
$R^2$=$R^3$=H, alkyl, in particular $CH_3$;

$R^4$=H, alkyl, in particular $CH_3$, alkyl (C=O), substituted alkyl (C=O), aryl (C=O), β-alanyl ($H_2NCH_2CH_2$ (C=O); α-amino-acyl;
$R^5$=alkyl, in particular methyl, phenyl;

The invention includes all the stereoisomers, diastereoisomers and enantiomers, in particular in terms of the carbon atom that bears the group COOH, taken alone or in a mixture.

It also includes all the salts of pharmaceutically acceptable acids of said compounds of general formula (I).

Among the compounds of general formula (I), the invention relates in particular to:
those characterized in that $R^4$ represents hydrogen, or the methyl group, or the acetyl group, or the benzoyl group, or the β-alanyl ($H_2NCH_2CH_2$ (C=O) group;
those prepared in the experimental part, in particular 1. L-5-acetylsulfanyl-histidine (Compound 1);
2. L-5-acctylsulfanyl-histidine-α,N,N(dimethyl)-histidine (Compound 2);
3. L-5-acetylsulfanyl-α,N,N,N(trimethyl)-histidine (Compound 3);
4. L-5-acetylsulfanyl-α,N(glycinyl)-histidine (Compound 4);
5. L-5-acetylsulfanyl-α,N,N(dimethyl)-1-methylhistidine (Compound 5);
6. L-5-acetylsulfanyl-α,N,N,N(trimethyl)-1-methylhistidine (Compound 6);
7. L-5-acetylsulfanyl-α,N(L-alanyl)-histidine (Compound 7);
8. L-5-acetylsulfanyl-α,N(pentanoyl)-histidine (Compound 8);
9. L-5-acetylsulfanyl-α,N(methyl)-histidine (Compound 9);
10. L-5-acetylsulfanyl-α,N(acetyl)-histidine (Compound 10);
11. L-5-acetylsulfanyl-α,N(benzoyl)-histidine (Compound 11);
12. L-5-acetylsulfanyl-α,N(β-alanyl)-histidine (Compound 12);
13. L-1-methyl-5-acetylsulfanyl-histidine (Compound 13);
14. L-5-benzoylsulfanyl-histidine (Compound 14);
15. L-5-benzoylsulfanyl-α,N,N(dimethyl)-histidine (Compound 15);
16. L-5-benzoylsulfanyl-α,N,N,N(trimethyl)-histidine (Compound 16);
17. L-5-acetylsulfanyl-α,N(L-phenylalanyl)-histidine (Compound 17).

Among the pharmaceutically acceptable acids, one can cite, in a nonlimiting manner, the mineral acids such as the hydrochloric, hydrobromic, hydroiodic, sulfuric, tartaric, phosphoric acids, or the organic acids such as the formic, acetic, trifluoroacetic, propionic, benzoic, maleic, fumaric, succinic, citric, oxalic, glyoxylic, aspartic acids and alkanesulfonic acids such as methanesulfonic, trifluoromethanesulfonic, ethanesulfonic acids, and arylsulfonic acids such as benzene- and paratoluenesulfonic acids.

In the above formula (I):
alkyl radical denotes a linear or cyclic, possibly branched, group comprising 1 to 6 carbon atoms,
substituted alkyl radical denotes an alkyl group substituted with one or more fluorine atoms, or substituted with an alkenyl group comprising one or more carbon-carbon double bonds, or substituted with one or more OH or SH or $NH_2$ or COOH functions, as well as the enantiomers thereof, and the diastereoisomers thereof.
aryl radical denotes an optionally fluorinated or polyfluorinated phenyl group, and comprising optionally one or more OH or SH or $NH_2$ or COOH functions
α-amino-acyl radical denotes the acyl radical of any proteogenic amino acid, that is to say any amino acid entering into the composition of proteins found in the plant or animal world, including man.

According to a second aspect, the invention also relates to a method A for preparing novel 5-acylsulfanyl-histidine compounds and their derivatives of general formula (I), given explicitly in the accompanying FIG. 1, and characterized in that it includes the following steps:

1) The reaction of the histidine, racemic (DL) or one of the enantiomers thereof (D or L), or
   one of their derivatives alkylated on the nitrogen in position 1 of the imidazole ring, racemic (DL) or one of the enantiomers thereof (D or L), or
   one of their derivatives alkylated or acylated on the nitrogen of the α-amine function, racemic (DL) or one of the enantiomers thereof (D or L), or
   one of their derivatives alkylated on the nitrogen in position 1 of the imidazole ring and alkylated or acylated on the nitrogen of the α-amine function, racemic (DL) or one of the enantiomers thereof (D or L),
in the presence of 1 to 2 equivalents of mineral or organic acid, with
   a) an agent generating halogenium ions $X^+$ in a polar protic solvent, at temperatures of 0-25° C., then with
   b) a sulfur-containing reagent of the carbothioic acid type of formula alkyl C(=O)SH or one of the salts thereof in a polar protic solvent,
2) then, optionally, the purification by column liquid chromatography or any other purification method well known to the person skilled in the art.

According to a particular embodiment of the method A according to the invention: the agent generating halogenium ions $X^+$ can be:
   a) bromine $Br_2$ (as commercial reagent or prepared in situ); or
   b) NBS or any N-bromo-imide and N-bromo-amide derivative According to another particular embodiment of this method A according to the invention, the polar protic solvent can be water or an aqueous solution.

According to yet another particular embodiment of the method A according to the invention, the sulfur-containing reagent of the carbothioic acid type can be, for example, thioacetic acid; or thiobenzoic acid, or mixtures thereof.

According to another particular embodiment of the method A according to the invention, the sulfur-containing reagent of the carbothioic acid salt type can be, for example, potassium thioacetate, optionally in a mixture with an above-mentioned carbothioic acid.

According to yet another particular embodiment of this method A according to the invention, the temperature will be 0-5° C.

The innovating character of this method A is based on a novel reaction of direct introduction of an acylsulfanyl RC(=O)S group in position 5 of the imidazole ring of the histidine or of one of its derivatives, without the use of a protective group and in water as reaction solvent. This is particularly surprising given that, under the same operating conditions, the use of cysteine instead of carbothioic acid leads to an introduction of sulfur in position 2 of the imidazole ring, as shown in the patent U.S. Ser. No. 13/121, 891 and the patent U.S. Ser. No. 13/500,887 A1.

According to a third aspect, the present invention relates to the use of the above-mentioned 5-acylsulfanyl compounds of formula (I) or their derivatives, for the preparation of corresponding 5-sulfanylhistidine compounds and their disulfides described below.

According to a fourth aspect, the invention covers novel 5-sulfanylhistidine compounds and their derivatives having the following general formula (II):

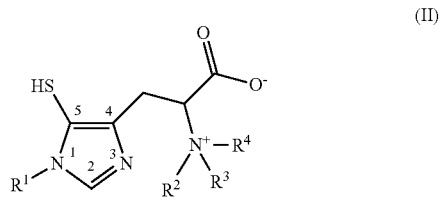

Where:
$R^1$ to $R^4$ are as defined for the radicals $R^1$ to $R^4$ of formula (I), in particular: $R^1$=H, alkyl, in particular $CH_3$; $R^2$=$R^3$=H, alkyl, in particular $CH_3$;
$R^4$=H, alkyl, in particular $CH_3$, alkyl (C=O), substituted alkyl (C=O), aryl (C=O), β-alanyl ($H_2NCH_2CH_2$ (C=O); α-amino-acyl;
being understood that when $R^1$=H then $R^2$, $R^3$ and $R^4$ cannot be H simultaneously.

The invention includes all the stereoisomers, diastereoisomers and enantiomers, in particular in terms of the carbon atom bearing the COOH group, as well as all the corresponding disulfides, taken separately or in a mixture.

It also includes all the salts of pharmaceutically acceptable acids of said compounds of general formula (II).

Among the compounds of general formula (II), the invention relates in particular to:
   those characterized in that $R^4$ represents hydrogen, or the methyl group, or the acetyl group, or the benzoyl group, or the β-alanyl ($H_2NCH_2CH_2$ (C=O) group;
   those prepared in the experimental part, in particular:
1. the disulfide of L-5-sulfanyl-α,N(methyl)-histidine (Compound 22);
2. L-5-sulfanyl-α,N(methyl)-histidine (Compound 23);
3. the disulfide of L-5-sulfanyl-α,N,N(dimethyl)-histidine (Compound 24);
4. L-5-sulfanyl-α,N,N(dimethyl)-histidine (Compound 25);
5. L-5-sulfanyl-α,N,N,N(trimethyl)-histidine (Compound 26);
6. the disulfide of L-5-sulfanyl-α,N,N,N(trimethyl)-histidine (Compound 27);
7. the disulfide of L-5-sulfanyl-α,N(acetyl)-histidine (Compound 28);
8. L-5-sulfanyl-α,N(acetyl)-histidine (Compound 29);
9. L-5-sulfanylcarnosine (Compound 30);
10. the disulfide of iso-ovothiol A (Compound 31);
11. iso-ovothiol A (Compound 32);
12. the disulfide of L-5-sulfanyl-α,N,N(dimethyl)-1-methylhistidine (Compound 33);
13. L-5-sulfanyl-α,N,N,N(trimethyl)-1-methylhistidine (Compound 34);
14. L-5-sulfanyl-α,N(L-alanyl)-histidine (Compound 35);
15. the disulfide of 5-sulfanyl-α,N(pentanoyl)-histidine (Compound 36).

Among the pharmaceutically acceptable acids, one can cite, in a nonlimiting manner, the mineral acids such as hydrochloric, hydrobromic, hydroiodic, sulfuric, tartaric, phosphoric acids or the organic acids such as the formic, acetic, trifluoracetic, propionic, benzoic, maleic, fumaric, succinic, citric, oxalic, glyoxylic, aspartic acids, alkanesulfonic acids such as methanesulfonic, trifluoromethanesulfonic, ethanesulfonic acids, the arylsulfonic acids such as benzene- and paratoluenesulfonic acids.

In formula (II) above:
alkyl radical denotes a linear or cyclic, optionally branched, group comprising 1 to 6 carbon atoms
substituted alkyl radical denotes an alkyl group substituted with one or more fluorine atoms, or substituted with an alkenyl group comprising one or more carbon-carbon double bonds, or substituted with one or more OH or SH or $NH_2$ or COOH functions, as well as the enantiomers thereof, and the diastereoisomers thereof.
aryl radical denotes an optionally fluorinated or polyfluorinated phenyl group, and comprising optionally one or more OH or SH or $NH_2$ or COOH functions
α-amino-acyl radical denotes the acyl radical of any proteogenic amino acid, that is to say any amino acid entering into the composition of the proteins found in the plant or animal world, including man.
disulfide denotes any compound obtained by oxidation between two identical molecules of derivatives of the 5-sulfanylhistidine type described in the invention.

The novel 5-sulfanylhistidine compounds and their derivatives having the general formula (II) as well as their disulfides could prove to be nutritional, cosmetic or medicinal active substances.

According to a fifth aspect, the invention furthermore relates to a method B for preparing the 5-sulfanylhistidine compounds and their derivatives of general formula (II) obtained from 5-acylsulfanyl-histidine compounds and their derivatives of general formula (I) described in the method A above, and characterized in that it includes the following steps:

1) Either directly (method B1):
a) by hydrolysis of the 5-acylsulfanyl-histidine derivatives obtained according to the invention in a polar protic solvent by stirring at a temperature above 20° C. in the presence of a thiol,
b) then, optionally, purification by column liquid chromatography or any other purification method well known to the person skilled in the art.

2) Or indirectly (method B2):
a) by hydrolysis of the 5-acylsulfanyl-histidine derivatives obtained according to the invention in a polar protic solvent by stirring at a temperature above 20° C. in order to obtain the corresponding disulfide,
b) then reduction of the disulfide by reaction with a thiol,
c) then, optionally, purification by column liquid chromatography or any other purification method well known to the person skilled in the art.

According to a particular implementation of this method B according to the invention, the polar protic solvent can be water or an aqueous solution.

According to another particular implementation of the method B according to the invention, the thiol can be, for example, mercaptopropionic acid or dithiothreitol, or mixtures thereof.

According to yet another particular implementation of this method B according to the invention, the temperature can be between 20 and 130° C.

By this aspect, the applicant demonstrates the ability of the compounds of general formula (I) to be precursors of 5-sulfanylhistidine compounds and their derivatives of general formula (II) after hydrolysis.

According to a sixth aspect, the invention also relates to a method C for preparing disulfides of the 5-sulfanylhistidines and of their derivatives:

1) either directly from the 5-acylsulfanyl-histidine compounds and their derivatives of general formula (I), characterized in that it includes the following steps:

a) hydrolysis of the 5-acylsulfanyl-histidine derivatives of general formula (I) obtained according to the invention in a polar protic solvent by stirring in air and at a temperature above 20° C. in order to obtain the corresponding disulfide,
b) then, optionally, purification by column liquid chromatography or any other purification method well known to the person skilled in the art;

2) or from 5-acylsulfanyl-histidines and their derivatives of general formula (II), characterized in that it includes the following steps:
a) oxidation by oxygen or dimethyl sulfoxide or any other oxidation method well known to the person skilled in the art,
b) then, optionally, purification by column liquid chromatography or any other purification method well known to the person skilled in the art.

By this aspect, the applicant demonstrates the ability of the 5-acylsulfanyl-histidine compounds of general formula (I) to be precursors of disulfides of 5-sulfanylhistidines and of their derivatives after hydrolysis and oxidation.

According to a seventh aspect, the invention also relates to a "one-pot" method D for preparing the 5-sulfanylhistidine derivatives and the corresponding disulfides thereof from corresponding histidine derivatives, by combining the methods A with B or with C, and characterized in that it includes the following steps:

in the presence of 1 to 2 equivalents of mineral or organic acid, the reaction with:
a) an agent generating halogenium ions $X^+$ in a polar protic solvent, at a temperature of 0-25° C., then with
b) a sulfur-containing reagent of the carbothioic acid type of formula alkyl C(=O)SH or one of the salts thereof in a polar protic solvent,
followed by
1) Either:
c) the hydrolysis of the 5-acylsulfanyl-histidine derivatives obtained in a polar protic solvent by stirring at a temperature between 70 and 130° C. in the presence of a thiol,
d) then, optionally, the purification by column liquid chromatography or any other purification method well known to the person skilled in the art.
2) Or:
d) by hydrolysis of the 5-acylsulfanyl-histidine derivatives obtained in a polar protic solvent by stirring at a temperature between 70 and 130° C. in order to obtain the corresponding disulfide,
e) then, optionally, purification by column liquid chromatography or any other purification method well known to the person skilled in the art.

DESCRIPTION OF THE FIGURES

The invention includes 4 figures.
FIG. 1: Scheme of the method for synthesizing compounds according to general formula (I)
FIG. 2: Representative spectrum ($H^1$ NMR, 400 MHz) of the reaction mixture obtained in Example 1, preparation of L-5-acetylsulfanyl-histidine (Compound 1)
FIG. 3: Representative spectrum ($H^1$ NMR, 400 MHz) of the reaction mixture obtained in Example 3, preparation of L-5-acetylsulfanyl-α,N,N(dimethyl)-histidine (Compound 2)
FIG. 4: Representative spectrum ($H^1$ NMR, 400 MHz) of the reaction mixture obtained in Example 5, preparation of L-5-acetylsulfanyl-α,N,N(trimethyl)-histidine (Compound 3)

DESCRIPTION OF THE EXAMPLES

The following examples as well as the scheme of the method of the invention (see FIG. 1) are provided only for illustration and are in no way capable of limiting the scope of the invention.

In the examples described below, the temperature is either ambient temperature or a temperature given in degree Celsius, and the pressure is atmospheric pressure, unless otherwise indicated.

The reagents used are commercially available from international suppliers such as SAF (France), Alfa Aesar, Fisher Scientific, TCI Europe, Bachem (Switzerland, AKOS (Germany) except for the following compounds: N-methylhistidine hydrochloride, N,N-dimethylhistidine hydrochloride hydrate and L-hercynine, which were prepared according to the cited protocols.

All the experiments are carried out in the ambient atmosphere unless indicated otherwise.

The $^1$H NMR analyses were recorded at 400 MHz or at 300 MHz in $D_2O$ or a $D_2O/DCl$ mixture, using the HOD signal (4.79 ppm) as internal reference. The chemical shifts are noted in ppm, and the multiplicity of the signals indicated by the following symbols: s (singlet), d (doublet), t (triplet), q (quartet), and m (multiplet). The coupling constants are recorded in hertz (Hz). The $^{13}$C NMR analyses are recorded at 75 MHz in $D_2O$ or $D_2O/DCl$. The mass analyses are obtained by chemical ionization at atmospheric pressure (APCI-MS). The melting points were measured using an apparatus from the company Stuart Scientific. The HPLC analyses were carried out on an Acquity apparatus (Waters), using two types of columns: A. Kromasil Diol column 250×4.6 (5 μm). The mobile phase used is a mixture of solvent A (10/90 $H_2O$/acetonitrile+0.05% TFA) and of solvent B (50/50 $H_2O$/acetonitrile+0.05% TFA), with a gradient varying over 10 minutes from 90% A to 100% B and at a flow rate of 1.2 mL/min. B. Column of the Thermo Hypercarb type 100×4.6 (5 m). The mobile phase used is a mixture of solvent A (100% H2O+0.2% HCOOH) and of solvent B (100% acetonitrile+0.2% HCOOH), with a gradient varying over 8 minutes from 100% A to 40% and a flow rate of 1 mL/min. The detection is carried out with a universal ELSD detector (Sedere).

I—Preparation of the 5-acylsulfanyl-histidine Derivatives as Precursors of the 5-sulfanylhistidines and their Disulfides In the first paragraph, examples are given of the preparation of the 5-acylsulfanyl-histidine derivatives by activation with dibromine or N-bromosuccinimide (NBS) and reaction of the intermediate formed with thioacetic acid.

In the second paragraph, examples are given of the use of these 5-acylsulfanyl derivatives, generally prepared in situ, as precursor of 5-sulfanylhistidines and their derivatives.

I.1. Preparation of the 5-acylsulfanyl-histidine Derivatives by Activation with Dibromine or with N-bromosuccinimide (NBS) and Reaction with Thioacetic Acid

Example 1: Preparation of L-5-acetylsulfanyl-histidine (Compound 1) by Activation with Dibromine and Reaction with Thioacetic Acid

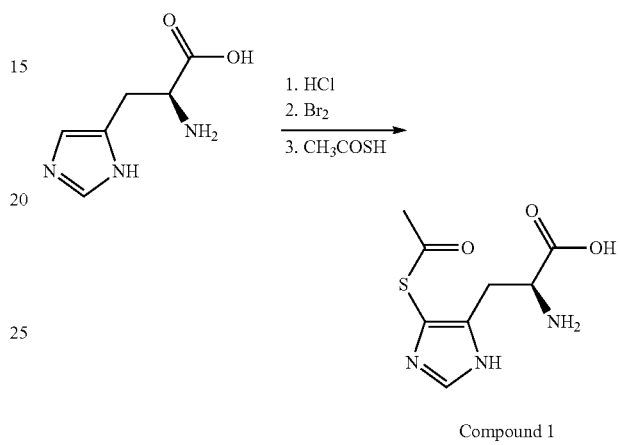

Compound 1

The hydrochloride of monohydrated L-histidine (52.93 g; 250 mmoles; 1 eq.) is dissolved in 1.5 L of demineralized water, then the solution is cooled to 0° C. in 30 minutes. Under strong stirring, dibromine (16.7 mL; 51.93 g; 325 mmoles; 1.3 eq.) is added dropwise very rapidly. The solution turns red. Thioacetic acid (73.3 mL; 78.46 g; 1 mole; 4 eq.) is added very rapidly: the solution immediately becomes decolorized and changes from red to light yellow. The vigorous stirring is maintained at 0° C. for 1 h.

Compound 1 is obtained with a reaction yield of 72 mol % as calculated from the $^1$H NMR spectrum.

$^1$H NMR ($D_2O$ pH ~1, 400 MHz) of a sample of the mixture: δ (ppm)=2.57 (s, 3H); 3.38 (dd, J=15.6 Hz and J=6.8 Hz, 1H); 3.47 (dd, J=15.6 Hz, J=7.8 Hz, 1H); 4.34 (dd, J=7.8 Hz and J=6.8 Hz, 1H); 8.94 (s, 1H).

A singlet corresponding to the excess of thioacetic acid is detected at 2.48 ppm, as are signals of low intensity corresponding to the side products such as the acetic acid detected at 2.0 ppm. A representative spectrum is included in FIG. 2.

LCMS (APCI): 228.0 [M–H]$^-$

Example 2: Preparation of L-5-acetylsulfanyl-histidine (Compound 1) by Activation with N-bromosuccinimide and Reaction with Thioacetic Acid

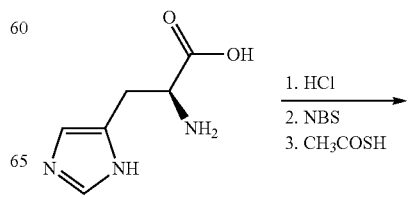

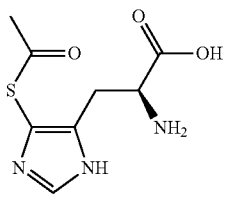

Compound 1

The hydrochloride of monohydrated L-histidine (10.48 g; 50 mmoles; 1 eq.) is dissolved in 300 mL of demineralized water containing a 37% concentrated hydrochloric acid solution (4.17 mL; 4.92 g; 50 mmoles; 1 eq.), then the solution is cooled to 0° C. Very strong stirring is maintained. N-Bromosuccinimide (11.56 g; 65 mmoles; 1.3 eq.) is added in a single portion: the mixture turns limpid orange after 30 seconds. The temperature rises to 1° C. After 2 minutes 30 seconds, thioacetic acid (14.7 mL; 15.69 g; 200 mmoles; 4 eq.) is added all at once: the decolorization occurs very rapidly. The temperature rises to 4° C. After cooling to 0° C., the vigorous stirring is maintained for 1 h.

Compound 1 is obtained with a reaction yield of 75 mol % as calculated from the $H^1$ NMR spectrogram (in the reaction mixture).

The $^1$H NMR and mass spectra are identical to those obtained in Example 1.

Example 3: Preparation of L-5-acetylsulfanyl-α,N,N(dimethyl)-histidine (Compound 2) by Activation with N-bromosuccinimide and Reaction with Thioacetic Acid

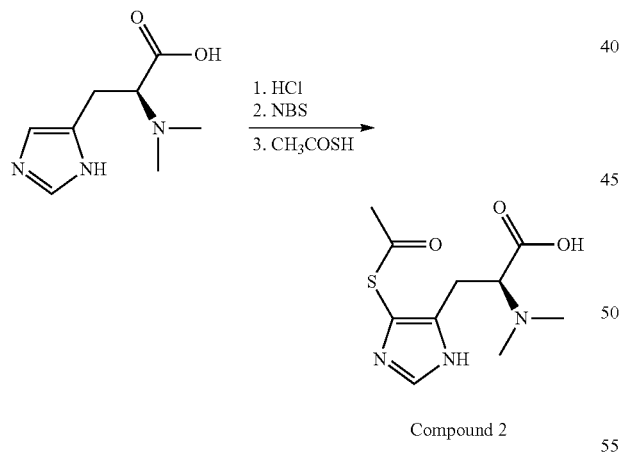

Compound 2

The hydrochloride of monohydrated α-N,N(dimethyl)-histidine (6.06 g; 25 mmoles; 1 eq.) (see V. N. Reinhold et al., J. Med. Chem. 1968, 11, 258-260) is dissolved in 135 mL of demineralized water. Then a 37% concentrated hydrochloric acid solution (2.1 mL; 2.46 g; 25 mmoles; 1 eq.) is added, and the resulting solution is cooled to 1° C. Very vigorous stirring is maintained. N-bromosuccinimide (2.31 g; 13 mmoles; 1.3 eq.) is added rapidly. After 1 minute, thioacetic acid (2.94 mL, 3.14 g; 40 mmoles; 4 eq.) is added very rapidly. Vigorous stirring is maintained at 0° C. for 30 minutes.

Compound 2 is obtained with a reaction yield of 70 mol % as calculated from the $^1$H NMR spectrogram.

$^1$H NMR (D$_2$O pH≈1, 400 MHz) of a sample of the mixture: δ (ppm)=2.57 (s, 3H); 2.79 (s, 6H); 3.42 (dd, J=14.9 Hz and J=10.6 Hz, 1H); 3.49 (dd, J=14.9 Hz and J=4.4 Hz, 1H); 4.20 (dd, J=10.6 Hz and J=4.4 Hz, 1H); 8.92 (s, 1H).

A singlet corresponding to the excess of thioacetic acid is detected at 2.47 ppm, as are signals of low intensity corresponding to the side products such as the acetic acid detected at 2.0 ppm. A representative spectrum is included in FIG. 3.

Compound 2 is purified on a silica column using an ethyl acetate/ethanol gradient followed by elution with water.

$^1$H NMR (D$_2$O pH 2-3, 300 MHz): δ (ppm)=2.54 (s, 3H); 2.96 (s, 6H); 3.28 (dd, J=14.7 Hz and J=10.4 Hz, 1H); 3.39 (dd, J=14.7 Hz, J=4.4 Hz, 1H); 3.87 (dd, J=10.4 Hz and J=4.4 Hz, 1H); 8.81 (s, 1H).

A singlet of low intensity corresponding to the hydrolyzed product (compound 18b) is detected at 8.33 ppm.

$^{13}$C NMR (D$_2$O, 75 MHz): δ (ppm)=22.4; 30.0; 41.7; 6.84; 117.2; 134.3; 136.8; 170.9; 195.9.

LCMS (APCI): 258.9 [M+H]$^+$

Example 4: Preparation of L-5-acetylsulfanyl-α,N,N(dimethyl)-histidine (Compound 2) by Activation with Dibromine and Reaction with Thioacetic Acid

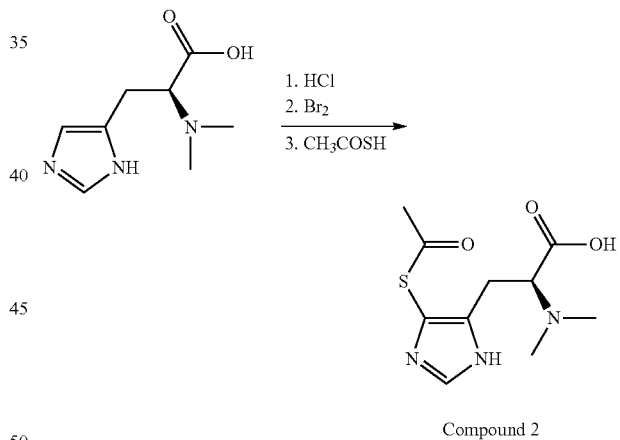

Compound 2

The hydrochloride of monohydrated α,N,N(dimethyl)histidine (1.66 g; 6.98 mmoles; 1 eq.) (see V. N. Reinhold et al., J. Med. Chem. 1968, 11, 258-260) is dissolved in 57 mL of demineralized water, then the solution is cooled to 0° C. Under strong stirring, dibromine (470 μL; 1.45 g; 9.08 mmoles; 1.3 eq.) is added dropwise in 3 minutes. The solution turns red. After 1 minute, thioacetic acid (2.56 mL; 2.74 g; 34.91 mmoles; 5 eq.) is added very rapidly: the solution immediately becomes decolorized and changes from red to clear yellow. Vigorous stirring is maintained at 0° C. for 1 h.

Compound 2 is obtained with a reaction yield of 69 mol % as calculated from the $^1$HNMR spectrogram.

The $^1$H NMR and mass spectra are identical to those obtained in Example 3.

Example 5: Preparation of L-5-acetylsulfanyl-α,N,N,N(trimethyl)-histidine (Compound 3) by Activation with N-bromosuccinimide and Reaction with Thioacetic Acid

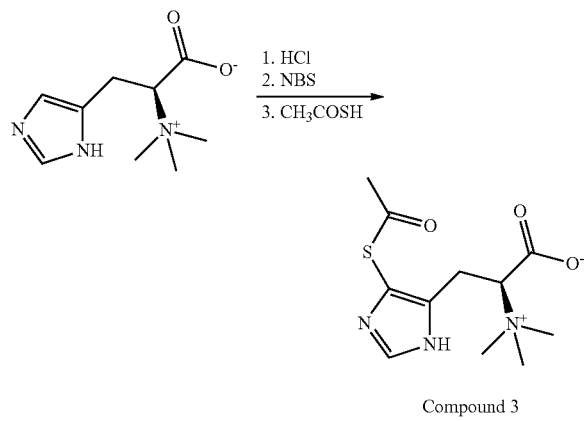

Compound 3

L-Hercynine (2.0 g; 9.96 mmoles; 1 eq.) (see V. N. Reinhold et al., J. Med. Chem. 1968, 11, 258-260) is dissolved in 55 mL of demineralized water. Then a 37% concentrated hydrochloric acid solution (1.66 mL; 1.96 g; 19.91 mmoles; 2 eq.) is added, and cooled to 0° C. Under strong stirring, N-bromosuccinimide (2.48 g; 13.94 mmoles; 1.4 eq.) is added: the solution turns red. After 5 minutes, thioacetic acid (4.4 mL; 4.69 g; 59.74 mmoles; 6 eq.) is added very rapidly. The stirring is maintained for 40 minutes.

Compound 3 is obtained with a reaction yield of 65 mol % as calculated from the $^1$H NMR spectrogram.

$^1$H NMR (D$_2$O, pH=1, 400 MHz) of a sample of the mixture: δ (ppm): 2.53 (s, 3H); 3.33 (s, 9H); 3.50 (m, 2H); 4.13 (m, 1H); 8.91 (s, 1H).

Two singlets corresponding to the excess of thioacetic acid and to the succinimide are at 2.44 ppm and 2.76 ppm, as are signals of low intensity corresponding to the side products such as the acetic acid detected at 2.0 ppm. A representative spectrum is included in FIG. 4.

The product is purified on a silica column (ethyl acetate/ethanol/water gradient).

$^1$H NMR (D$_2$O, pH 2-3, 400 MHz): δ (ppm)=2.53 (s, 3H); 3.30 (s, 9H); 3.37 (m, 1H); 3.44 (dd, J=14.0 Hz and J=3.8 Hz, 1H); 3.88 (dd, J=11.7 Hz and J=3.8 Hz, 1H); 8.72 (s, 1H).

$^{13}$C NMR (D$_2$O, 75 MHz): δ (ppm)=22.9; 30.0; 52.5; 76.5; 117.9; 133.1; 137.2; 169.7; 196.0.

LCMS (APCI): 272.1 [M+H]$^-$

Example 6: Preparation of L-5-acetylsulfanyl-α,N,N,N(trimethyl)-histidine (Compound 3) by Activation with Bromine and Reaction with Thioacetic Acid

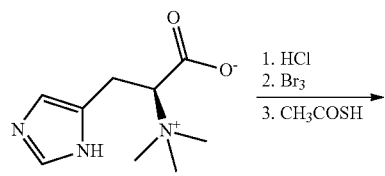

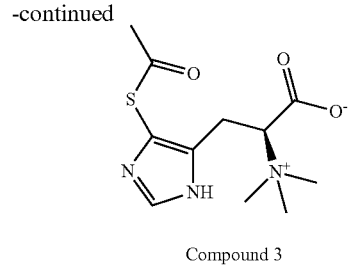

Compound 3

L-Hercynine (1.0 g, 5 mmoles; 1 eq.) is dissolved in 35 mL of demineralized water. Then a 37% concentrated hydrochloric acid solution (417 μL; 5 mmoles; 1 eq.) is added, and the solution is cooled to 1° C. Under strong stirring, dibromine (0.33 mL; 1.03 g, 6.5 mmoles; 1.3 eq.) is added: a red gum forms in a first phase and dissolves after 30 minutes. After 4 minutes, thioacetic acid (2.20 mL; 2.68 g; 25 mmoles; 10 eq.) is added very rapidly. The stirring is continued for 30 minutes.

Compound 3 is obtained with a reaction yield of 68 mol % as calculated from the $^1$H NMR spectrogram.

The $^1$H NMR and mass spectra are identical to those obtained in Example 5.

Example 7: Preparation of L-5-acetylsulfanyl-α,N(glycinyl)-histidine (Compound 4) by Activation with N-bromosuccinimide and Reaction with Thioacetic Acid

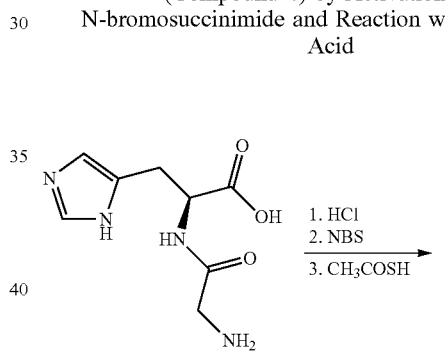

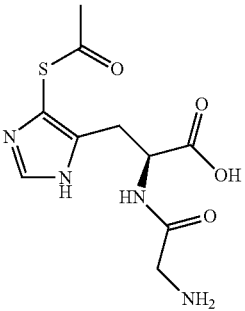

Compound 4

α,N(Glycinyl)-histidine (212 mg, 1 mmole; 1 eq.) is dissolved in 7 mL of demineralized water and 1 mL of acetonitrile. Then a 37% concentrated hydrochloric acid solution (170 μL, 2 mmoles; 2 eq.) is added, and the solution is cooled to 0° C. Under strong stirring, N-bromosuccinimide (230 mg, 1.3 mmoles; 1.3 eq.) is added. After 3 minutes, thioacetic acid (370 μL, 5.0 mmoles; 5 eq.) is added very rapidly. Stirring is maintained at 0° C. for 30 minutes.

Compound 4 is obtained with a reaction yield of 62 mol % as calculated from the $^1$H NMR spectrogram.

$^1$H NMR (D$_2$O, pH ~1, 400 MHz) of a sample of the mixture: δ (ppm)=2.53 (s, 3H), 3.20 (dd, J=15.3 Hz and J=8.5 Hz, 1H), 3.36 (dd, J=15.3 Hz and J=5.7 Hz, 1H), 3.79 (dd, J=16.4 Hz and J=10.7 Hz, 2H); 3.84 (m, 1H), 8.86 (s, 1H).

A singlet corresponding to the excess of thioacetic acid is detected at 2.48 ppm, a singlet at 2.78 ppm corresponding to the succinimide is detected as are signals of low intensity corresponding to the side products, such as the acetic acid detected at 2.0 ppm.

LCMS (APCI): 287.3 [M+H]+

Example 8: Preparation of the L-5-acetylsulfanyl-α,N,N(dimethyl)-1-methylhistidine Derivative (Compound 5) by Activation with N-bromosuccinimide and Reaction with Thioacetic Acid a) Preparation of α,N,N(dimethyl)-1-methyl-L-histidine α,N,N(Dimethyl)-1-methyl-L-histidine is prepared by analogy with the protocol described for α,N,N(dimethyl)-L-histidine (V. N. Reinhold et al., J. Med. Chem. 1968, 11, 258-260) from 1-methyl-L-histidine and formaldehyde by reducing amination in the presence of palladium on activated charcoal (88%).

$^1$H NMR (D$_2$O, 400 MHz): δ (ppm)=2.91 (s, 6H); 3.18 (d, J=6.4 Hz, 2H); 3.66 (s, 3H); 3.85 (t, J=6.4 Hz, 1H); 6.96 (s, 1H); 7.57 (s, 1H).

b) Preparation of the L-5-acetylsulfanyl-α,N,N(dimethyl)-1-methylhistidine Derivative

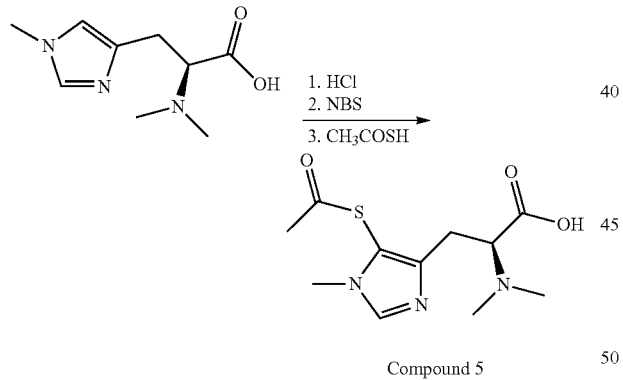

Compound 5

α,N,N(dimethyl)-1-methylhistidine (604 mg, 3 mmoles; 1 eq.) is dissolved in 22 mL of demineralized water. 37% Concentrated hydrochloric acid (250 μL, 3 mmoles; 1 eq.) is added, then the solution is cooled to 0° C. Very strong stirring is maintained. N-Bromosuccinimide (700 mg, 3.9 mmoles; 1.3 eq.) is added rapidly. After 3 minutes, thioacetic acid (1.1 mL, 15 mmoles; 5 eq.) is added very rapidly. Vigorous stirring is maintained at 0° C. for 30 minutes.

Compound 5 is obtained with a reaction yield of 65 mol % as calculated from the $^1$H NMR spectrogram.

$^1$H NMR (D$_2$O, pH ~1, 400 MHz) of a sample of the mixture: δ (ppm)=2.58 (s, 3H), 3.00 (s, 6H), 3.38 (dd, J=14.9 Hz and J=10.7 Hz, 1H), 3.46 (dd, J=14.9 Hz and J=4.3 Hz, 1H), 3.77 (s, 3H), 4.12 (dd, J=10.7 Hz and J=4.3 Hz, 1H), 8.97 (s, 1H)

A singlet corresponding to the excess of thioacetic acid is detected at 2.48 ppm, a singlet at 2.78 ppm corresponding to the succinimide is detected as are signals of low intensity corresponding to the side products such as acetic acid detected at 2.0 ppm.

The product is purified on a silica column using an 2/2/1 ethyl acetate/ethanol/water gradient followed by elution with a 1/1 ethanol/water mixture. Compound 5 (48%) is obtained in the form of a transparent oil.

$^1$H NMR (D$_2$O, 400 MHz): δ (ppm)=2.56 (s, 3H); 2.95 (s, 6H); 3.25 (dd, J=15.0 Hz and J=9.0 Hz, 1H); 3.31 (dd, J=15.0 Hz and J=5.4 Hz, 1H); 3.69 (s, 3H); 3.86 (dd, J=9.0 Hz and J=5.4 Hz, 1H); 8.53 (s, 1H).

The signals of ethanol are detected at 1.18 ppm and 3.65 ppm.

LCMS (APCI): 272.3 [M+H]+

Example 9: Preparation of L-5-acetylsulfanyl-α,N,N,N(trimethyl)-1-methylhistidine (Compound 6) by Activation with N-bromosuccinimide and Reaction with Thioacetic Acid a) Preparation of 1-methyl-hercynine 1-Methyl-hercynine is prepared by analogy with the protocol described for hercynine (V. N. Reinhold et al., J. Med. Chem. 1968, 11, 258-260) from 1-methyl-dimethyl-L-histidine and iodomethane by quaternization in methanol (89%).

$^1$H NMR (D$_2$O, 400 MHz): δ (ppm)=3.19 (m, 2H); 3.28 (s, 9H); 3.67 (s, 3H); 3.89 (dd, J=10.6 Hz and 4.5 Hz, 1H); 6.94 (s, 1H); 7.57 (s, 1H).

b) Preparation of L-5-acetylsulfanyl-α,N,N,N(trimethyl)-1-methylhistidine (Compound 6)

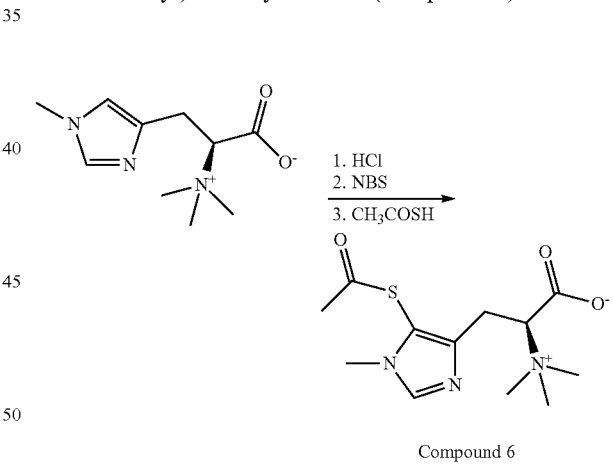

Compound 6

1-Methyl-hercynine (430 mg, 2 mmoles; 1 eq.) is dissolved in 15 mL of demineralized water. 37% concentrated hydrochloric acid (170 μL, 2 mmoles; 1 eq.) is added, then the solution is cooled to 0° C. Under strong stirring, N-bromosuccinimide (465 mg, 2.6 mmoles; 1.3 eq.) is added. After 3 minutes, thioacetic acid (740 μL, 10 mmoles; 5 eq.) is added very rapidly. The stirring is maintained at 0° C. for 30 minutes.

Compound 6 is obtained with a reaction yield of 67 mol % as calculated from the $^1$H NMR spectrogram.

$^1$H NMR (D$_2$O, pH ~1, 400 MHz) of a sample of the mixture: δ (ppm)=2.57 (s, 3H), 3.32 (s, 9H), 3.53 (m, 2H), 3.75 (s, 3H), 4.08 (dd, J=11.9 Hz and J=3.7 Hz, 1H), 8.98 (s, 1H).

A singlet corresponding to the excess of thioacetic acid is detected at 2.48 ppm, a singlet at 2.78 ppm corresponding to succinimide is detected as are signals of low intensity corresponding to the side products, such as acetic acid detected at 2.0 ppm.

LCMS (APCI): 286.0 [M+H]+

Example 10: Preparation of L-5-acetylsulfanyl-α-N (L-alanyl)-histidine (Compound 7) by Activation with N-bromosuccinimide and Reaction with Thioacetic Acid

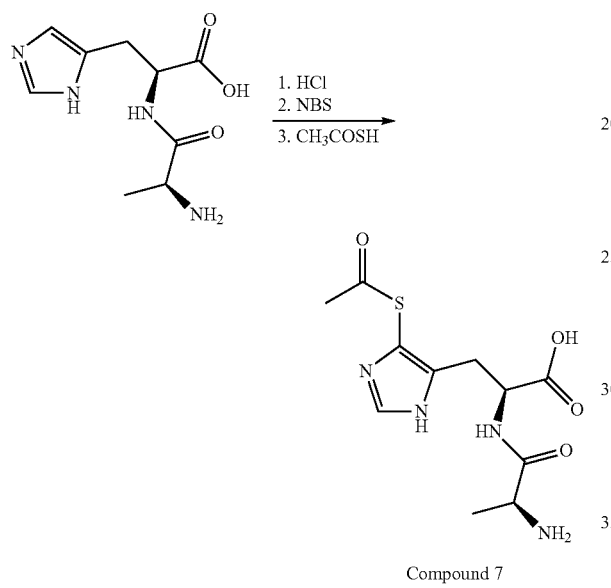

Compound 7

α-N(L-alanyl)-histidine (500 mg, 2.2 mmoles; 1 eq.) is dissolved in 15 mL of demineralized water containing a 37% concentrated hydrochloric acid solution (370 µL, 4.4 mmoles; 2 eq.), then the solution is cooled to 0° C. N-Bromosuccinimide (510 mg, 2.9 mmoles; 1.3 eq.) is added in one portion: the mixture turns limpid orange after 30 seconds. After 3 minutes, thioacetic acid (820 µL, 11.0 mmoles; 5 eq.) is added very rapidly. Vigorous stirring is maintained at 0° C. for 30 minutes.

Compound 7 is obtained with a reaction yield of 65 mol % as calculated from the $^1$H NMR spectrogram of a sample.

The reaction mixture is washed with 2×25 mL of ethyl acetate, then the compound is purified on a silica column (ethyl acetate/ethanol/water 2/2/1). Compound 7 (410 mg, 54%, purity 88%) is obtained in the form of a transparent oil.

$^1$H NMR (D$_2$O, acid pH, 400 MHz): δ (ppm)=1.49 (d, J=7.2 Hz, 3H); 2.53 (s, 3H); 3.20 (dd, J=15.3 Hz and J=8.9 Hz, 1H); 3.36 (dd, J=15.3 Hz and J=5.8 Hz, 1H), 4.01 (q, J=7.2 Hz, 1H); 4.77 (m superposed over HOD signal); 8.86 (s, 1H).

A singlet corresponding to the succinimide is detected at 2.68 ppm.

LCMS (APCI): 301.1 [M+H]+

Example 11: Preparation of the 5-acetylsulfanyl-α,N(pentanoyl)-histidine Derivative (Compound 8) by Activation with N-bromosuccinimide and Reaction with Thioacetic Acid

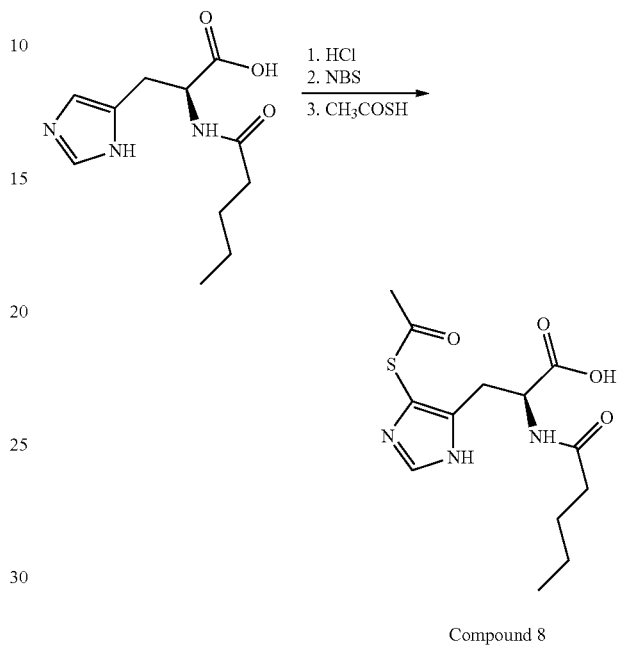

Compound 8

α,N(pentanoyl)-histidine (450 mg, 1.43 mmoles; 1 eq.) is dissolved in 10 mL of demineralized water containing a 37% concentrated hydrochloric acid solution (120 µL, 1.43 mmoles; 1 eq.), then the solution is cooled to 0° C. Very strong stirring is maintained. N-Bromosuccinimide (330 mg, 1.86 mmoles; 1.3 eq.) is added. After 3 minutes, thioacetic acid (530 µL, 7.15 mmoles; 5 eq.) is added very rapidly. Vigorous stirring is maintained at 0° C. for 30 minutes.

Compound 8 is obtained with a reaction yield of 67 mol % as calculated from the $^1$H NMR spectrogram of a sample.

The product is purified on a silica column (mixture 90% of ethyl acetate/ethanol 3/1 and 10% of water). 5-Acetylsulfanyl-α,N(pentanoyl)-histidine (compound 8) is obtained in the form of a transparent oil (320 mg, 64%, purity 90%).

$^1$H NMR (D$_2$O ~1, 400 MHz): δ (ppm): 0.85 (t, J=7.3 Hz, 3H); 1.17 (h, J=7.4 Hz, 2H); 1.47 (p, J=7.4 Hz, 2H); 2.22 (t, J=7.4 Hz, 2H); 2.55 (s, 3H); 3.17 (dd, J=15.2 Hz and J=9.6 Hz, 1H); 3.37 (dd, J=15.2 Hz and J=5.2 Hz, 1H); 4.79 (m superposed over HOD signal); 8.88 (s, 1H).

LCMS (APCI): 314.1 [M+H]+

To illustrate the invention, compounds 9-17 are prepared (Examples 12-21) by analogy with the preceding examples. The results, as well as the spectral characteristics, are summarized in Table 1 below.

TABLE 1

Examples 12-21 describing the preparation of Compounds 9-17 according to the invention. The compound formulas follow the table.

| Ex. No. | Formed product | by analogy with | Reagent | % conversion to desired product | $^1$H NMR: Characteristic signals | | | LC-MS [M + H]+ |
|---|---|---|---|---|---|---|---|---|
| | | | | | δ H-2 | δ α-H | δ AcS | |
| Ex. 12 | Compound 9 | Ex. 2 | NBS | 78% | 8.91 | 4.13 (dd, J = 7.7 Hz, J = 5.6 Hz) | 2.55 | 244.1 |
| Ex. 13 | Compoun 10 | Ex. 2 (1 eq. HCl) | NBS | 65% | 8.83 | 4.73 (m) | 2.51 | 272.1 |
| Ex. 14 | Compound 11 | Ex. 2 (1 eq. HCl) | NBS | 58% | 8.85 | 4.93 (dd, J = 9.3 Hz, J = 4.7 Hz) | 2.56 | 334.1 |
| Ex. 15 | Compound 12 | Ex. 2 | NBS | 63% | 8.84 | 4.66 (m) | 2.51 | 301.0 |
| Ex. 16 | Compound 13 | Ex. 2 | NBS | 63% | 9.00 | 4.31 (dd, J = 7.6 Hz, J = 6.9 Hz) | 2.58 | 244.6 |
| Ex. 17 | | Ex. 1 | Br2 | 55% | | | | |
| Ex. 18 | Compound 14 | Ex. 2 (water/CH3CN) | NBS | 31% | 8.98 | 4.37 | — | 292.1 |
| Ex. 19 | Compound 15 | Ex. 2 (water/CH3CN) | NBS | 12% | 8.95 | 4.28 | — | 320.9 |
| Ex. 20 | Compound 16 | Ex. 2 (water/CH3CN) | NBS | 12% | 9.06 | 4.32 | — | 334.1 |
| Ex. 21 | Compound 17 | Ex. 2 | NBS | 40% | 8.89 | 4.36 | 2.58 | 377.2 |

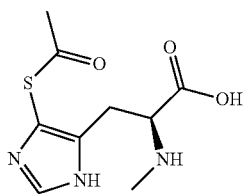 [SMILES: CN[C@@H](Cc1[nH]cnc1SC(C)=O)C(=O)O]

Compound 9

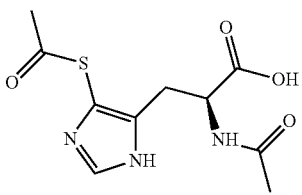 [SMILES: CC(=O)N[C@@H](Cc1[nH]cnc1SC(C)=O)C(=O)O]

Compound 10

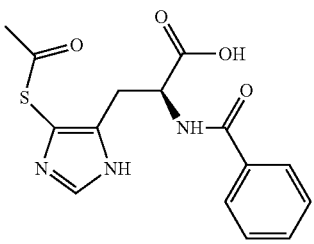 [SMILES: CC(=O)Sc1nc[nH]c1C[C@H](NC(=O)c1ccccc1)C(=O)O]

Compound 11

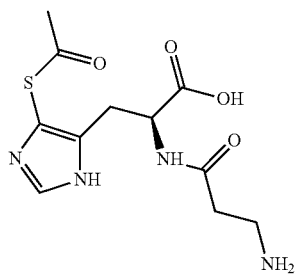

Compound 12

TABLE 1-continued

Examples 12-21 describing the preparation of Compounds 9-17 according to the invention.
The compound formulas follow the table.

| Ex. No. | Formed product | by analogy with | Reagent | % conversion to desired product | ¹H NMR: Characteristic signals δ H-2 | δ α-H | δ AcS | LC-MS [M + H]+ |
|---|---|---|---|---|---|---|---|---|

Compound 13

Compound 14

Compound 15

Compound 16

Compound 17

II. Application Examples

II.1 Transformation of the 5-acylsulfanyl Derivatives Prepared In Situ into Corresponding 5-sulfanylhistidine Derivatives by Hydrolysis To illustrate the application of the 5-acylsulfanyl-histidine derivatives according to the invention, in a nonlimiting manner, application examples are given in this paragraph of the novel 5-acylsulfanyl-histidine derivatives, generally prepared in situ, as precursor of 5-sulfanylhistidines and their derivatives.

These examples illustrate the usefulness of the novel 5-acylsulfanyl derivatives described in the invention for easily preparing 5-sulfanylhistidine compounds and their derivatives such as the disulfides, which, furthermore, are very difficult to prepare and require multistep syntheses.

In order to obtain better yields of 5-sulfanylhistidine derivatives, the 5-acylsulfanyl compounds are prepared in situ, then hydrolyzed directly thereafter, by stirring the reaction medium, preferably while heating the reaction medium. The presence of a thiol, such as mercaptopropionic acid or dithiothreitol, proves to be useful for the easy isolation of the 5-sulfanylhistidine derivatives, but it is not needed at all for the hydrolysis itself, as demonstrated in the follow-up examples 18d, 19b and 19c.

Example 22: "One Pot" Preparation of L-5-sulfanylhistidine Via In-Situ Preparation of 5-acetylsulfanylhistidine Followed by Hydrolysis (Compound 18)

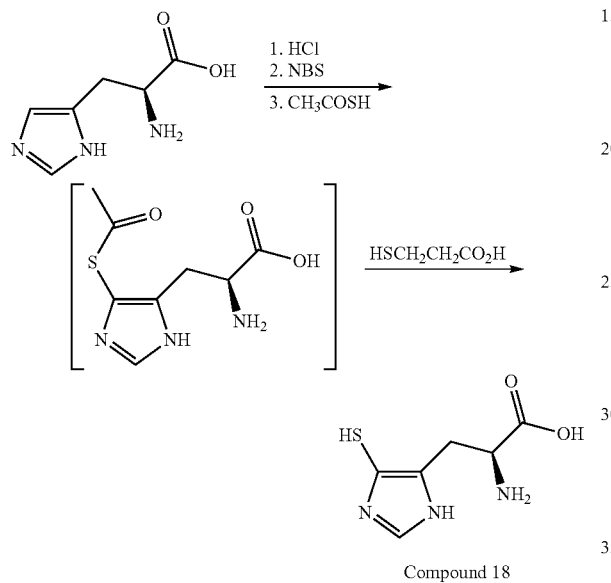

Compound 18

The hydrochloride of monohydrated L-histidine (10.48 g; 50 mmoles; 1 eq.) is dissolved in 300 mL of demineralized water and hydrochloric acid concentrated at 37% (4.17 mL; 4.92 g; 50 mmoles; 1 eq.), then the solution is cooled to 0° C. Very strong stirring is maintained. N-Bromosuccinimide (11.56 g; 65 mmoles; 1.3 eq.) is added in a single portion: the mixture becomes limpid orange. Thioacetic acid (14.7 mL; 15.69 g; 200 mmoles; 4 eq.) is added all at once. Vigorous stirring is maintained at 0° C. for 1 h. 3-Mercaptopropionic acid (26 mL; 32.2 g; 300 mmoles; 6 eq.) is added, then the slightly yellow solution is heated at 90° C. for 18 h. The solution is extracted with three times 300 mL of ethyl acetate. After neutralization and crystallization in the presence of dithiothreitol (231 mg; 1.5 mmoles; 0.03 eq.), the desired compound 18 crystallizes. The solid is filtered and dried under a vacuum to yield 2.97 g (31%; 41% with respect to the quantity of the intermediate SAc) of L-5-sulfanylhistidine (Compound 18) in the form of an off-white solid.

$^1$H NMR (D$_2$O, 400 MHz): δ (ppm)=3.18 (dd, J=15.8 Hz, J=7.3 Hz, 1H); 3.26 (dd, J=15.8 Hz and J=5.1 Hz, 1H); 4.33 (dd, J=7.3 Hz, J=5.1 Hz, 1H); 8.25 (s, 1H).

$^1$H NMR (D$_2$O+DCl, 400 MHz): δ (ppm)=3.11 (dd, J=15.1 Hz, J=6.5 Hz, 1H); 3.19 (dd, J=15.1 Hz and J=6.6 Hz, 1H); 4.12 (t, J=7.0 Hz, 1H); 8.37 (s, 1H).

$^{13}$C NMR (D$_2$O+DCl, 75 MHz): δ (ppm)=26.3; 55.2, 122.1; 130.1; 135.5; 173.6.

LC-MS (AP-): 186.0 [M−H]$^-$

[α]$_D$=+7.4° (c=0.1; 1N HCl)

Elemental analysis: C$_6$H$_9$N$_3$O$_2$S; Theoretical: C, 38.49%; H, 4.84% N, 22.44; Measured: C, 38.0%; H, 4.96%; N, 22.06.

Example 23: "One Pot" Preparation of D-5-sulfanylhistidine Via In-Situ Preparation of 5-acetylsulfanyl-histidine Followed by Hydrolysis (Compound 19)

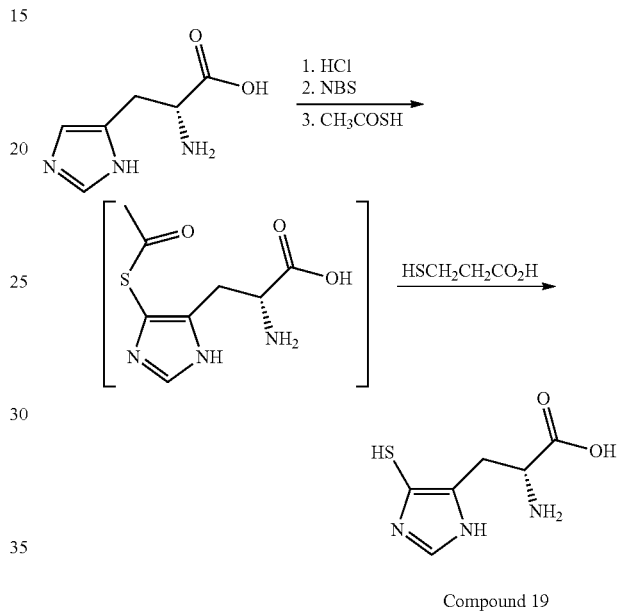

Compound 19

D-Histidine (3.92 g; 25 mmoles; 1 eq.) is dissolved in 150 mL of demineralized water and a hydrochloric acid solution concentrated at 37% (4.17 mL; 4.92 g; 50 mmoles; 2 eq.), then the solution is cooled to 0° C. Very strong stirring is maintained. N-Bromosuccinimide (5.78 g; 32.5 mmoles; 1.3 eq.) is added all at once: the solution turns limpid orange. Thioacetic acid (7.33 mL; 7.85 g; 200 mmoles; 4 eq.) is added all at once. Vigorous stirring is maintained at 0° C. for 1 h. 3-Mercaptopropionic acid (13 mL; 16.1 g; 150 mmoles; 6 eq.) is added, then the solution is heated at 100° C. for 18 h. After cooling, the solution is extracted with three times 150 mL of ethyl acetate. Dithiothreitol (13 mL; 16.1 g; 150 mmoles; 6 eq.) is added to the aqueous phase. After recrystallization in the presence of activated charcoal, the yield consists of 1.25 g of D-5-sulfanylhistidine (Compound 19) (26%; 35% with respect to the quantity of the intermediate SAc) in the form of a beige solid.

The $^1$H NMR, $^{13}$C NMR and mass spectra are identical to those obtained in Example 13 for Compound 9.

[α]$_D$: −7.1° (c=0.1; 1N HCl)

Example 24: "One Pot" Preparation of D,L-5-sulfanylhistidine Via In-Situ Preparation of 5-acylsulfanyl-histidine Followed by Hydrolysis (Compound 20)

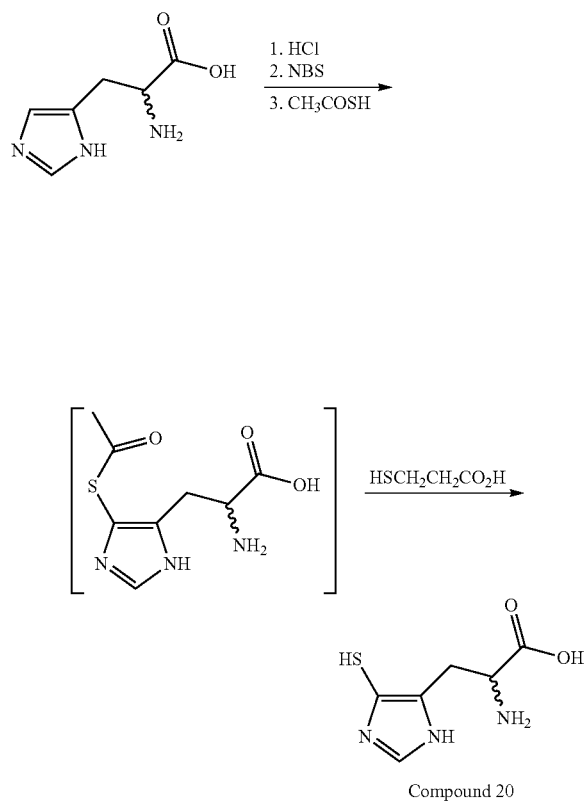

II.2 Transformation of the 5-acylsulfanyl Derivatives Prepared In Situ into Corresponding 5,5'-disulfane-diyl-bis-histidine Derivatives (Disulfides) by Hydrolysis

Example 25: "One Pot" Preparation of the Disulfide of L-5-sulfanylhistidine Via In-Situ Preparation of 5-acylsulfanyl-histidine Followed by Hydrolysis and Oxidation (Compound 21)

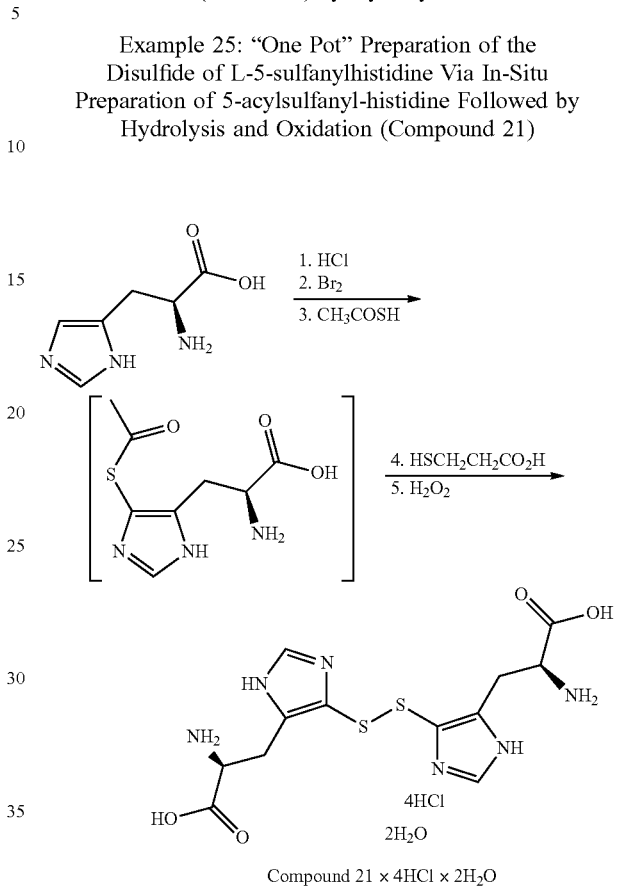

The hydrochloride of monohydrated DL-histidine (3.21 g; 15 mmoles; 1 eq.) is dissolved in 100 mL of demineralized water and a 37% concentrated hydrochloric acid solution (1.25 mL; 1.48 g; 15 mmoles; 1 eq.), then the solution is cooled to 0° C. Under very strong stirring, N-bromosuccinimide (3.47 g; 19.5 mmoles; 1.3 eq.) is added all at once. After 2 minutes, thioacetic acid (4.4 mL; 4.71 g; 60 mmoles; 4 eq.) is added all at once. Stirring is continued at 0° C. for 1 h. 3-Mercaptopropionic acid (8.0 mL; 9.65 g; 90 mmoles; 6 eq.) is added, then the solution is heated at 100° C. for 18 h. A precipitate corresponding to the disulfide of thioacetic acid and of mercaptopropionic acid is eliminated by filtration. The filtrate is washed with two times 100 mL of ethyl acetate. After neutralization and crystallization in the presence of dithiothreitol (233 mg; 1.5 mmoles; 0.1 eq.), 650 mg of D,L-5-sulfanylhistidine (Compound 20) (23%, 29% with respect to the quantity of the intermediate SAc) are obtained in the form of a white solid.

The $^1$H NMR, $^{13}$C NMR and mass spectra are identical to those obtained in Example 22 for Compound 18.

The hydrochloride of monohydrated L-histidine (14.82 g; 70 mmoles; 1 eq.) is dissolved in 126 mL of demineralized water, then the solution is cooled to 0° C. Under strong stirring, dibromine (4.32 mL; 13.42 g; 84 mmoles; 1.2 eq.) is added dropwise very rapidly. The solution turns red. Thioacetic acid (18.0 mL; 19.2 g; 245 mmoles; 3.5 eq.) is added very rapidly. Vigorous stirring is maintained at 0° C. for 20 minutes. 3-Mercaptopropionic acid (25 mL; 29.71 g; 280 mmoles; 4 eq.) is added, and the solution is heated at 80° C. overnight. The solution is cooled, then extracted with 3 times 150 mL of ethyl acetate. After oxidation with a 30% oxygenated water solution (3.5 mL; 3.97 g; 35 mmoles; 0.5 eq.), followed by a purification on Dowex WX2 resin, the disulfide of L-5-sulfanylhistidine hydrated hydrochloride (Compound 21) (4.66 g; 24%; 37% with respect to the quantity of the intermediate SAc) is obtained in the form of a light gray powder.

$^1$H NMR (D$_2$O, 400 MHz): δ (ppm)=3.27 (m, 2×1H); 3.32 (m, 2×1H); 4.17 (dd, J=8.0 Hz, J=6.6 Hz, 2×1H); 8.87 (s, 2×1H).
LCMS (APCI): 373.0 [M+H]$^+$
[α]$_D$: +23.6° (c=0.1; 1N HCl)

Example 26 a) "One Pot" Preparation of the Disulfide of L-5-sulfanyl-α,N(methyl)-histidine (Compound 22) Via In-Situ Preparation of 5-acylsulfanyl-histidine Followed by Hydrolysis and Oxidation (Compound 22)

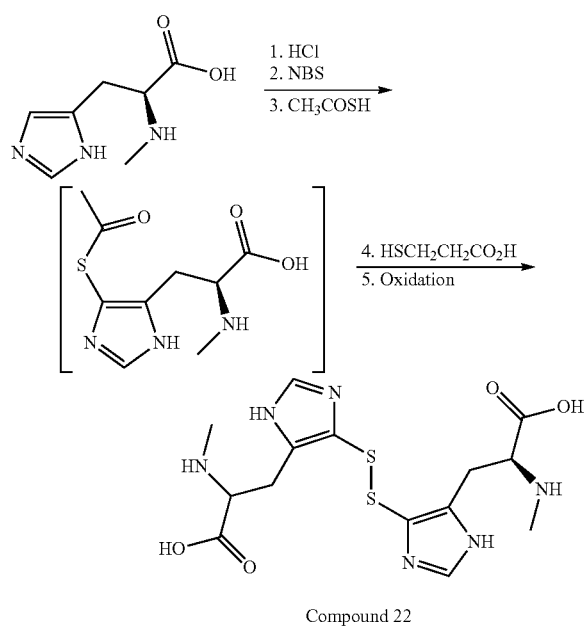

Compound 22

The hydrochloride of α,N(methyl)-L-histidine (1.05 g; 5 mmoles; 1 eq.) (V. N. Reinhold et al., J. Med. Chem. 1968, 11, 258-260) is dissolved in 35 mL of demineralized water containing a 37% concentrated hydrochloric acid solution; 420 µL (5 mmoles; 1 eq.), then the solution is cooled to 1° C. Very strong stirring is maintained. N-bromosuccinimide (1.17 g; 6.5 mmoles; 1.3 eq.) is added rapidly. Then thioacetic acid (2.57 mL; 2.74 g; 35 mmoles; 7 eq.) is added very rapidly. Vigorous stirring is maintained at 0° C. for 30 minutes. The solution is extracted with 40 mL of ethyl acetate, then 3-mercaptopropionic acid (2.2 mL; 2.65 g; 25 mmoles; 5 eq.) is added to the aqueous phase. The hydrolysis is carried out by heating at 100° C. for 20 h. After cooling of the solution, the reaction medium is extracted with 4 times 35 mL of ethyl acetate. After oxidation and purification on DOWEX 50WX2-400 resin, the disulfide of L-5-sulfanyl-α,N(methyl)-histidine (Compound 22) (620 mg, 61%, 75% with respect to the quantity of the intermediate SAc) is obtained in the form of a brown powder.

$^1$H NMR (MeOD/D$_2$O 20/1, 400 MHz): δ (ppm)=2.69 (s, 2×3H); 2.94 (dd, J=14.0 Hz, J=7.0 Hz, 2×1H); 2.99 (dd, J=14.0 Hz, J=5.0 Hz, 2×1H); 3.92 (dd, J=7.0 Hz, J=5.0 Hz, 2×1H); 7.79 (s, 2×1H).

LCMS (APCI): 401.0 [M+H]$^+$ b) Preparation of L-5-sulfanyl-α,N(methyl)-histidine by reduction of the disulfide (Compound 23)

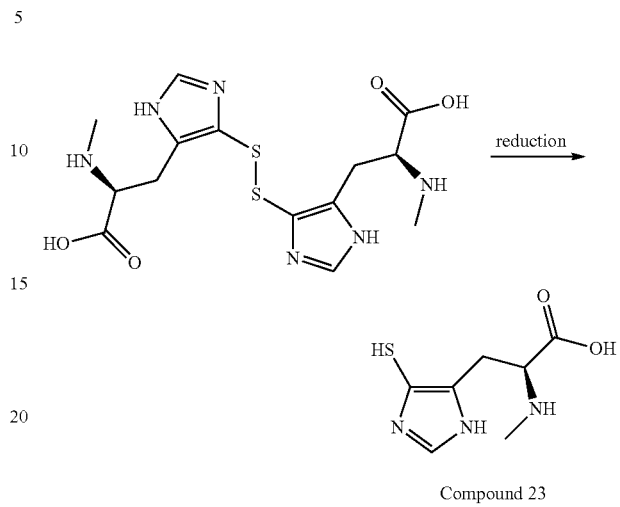

Compound 23

The disulfide of L-5-sulfanyl-α,N(methyl)-histidine (620 mg; 1.52 mmoles, 1 eq.) (Compound 22) is dissolved in 50 mL of water. The dithiothreitol (473 mg; 3.03 mmoles; 2 eq.) and the activated charcoal (300 mg) are added. The mixture is stirred for 4 h at ambient temperature. After filtration and crystallization in absolute ethanol, L-5-sulfanyl-α,N (methyl)-histidine (Compound 23) (351 mg, 56%) is obtained in the form of a beige powder.

$^1$H NMR (D$_2$O, 400 MHz): δ (ppm)=2.80 (s, 3H); 3.21 (dd, J=15.9 Hz, J=6.4 Hz, 1H); 3.28 (dd, J=15.9 Hz, J=5.2 Hz, 1H); 3.92 (m, 1H); 8.25 (s, 1H).

LCMS (APCI): 202.1 [M+H]$^+$

Example 27 a) "One Pot" Preparation of the Disulfide of L-5-sulfanyl-α,N,N(dimethyl)-histidine Via In-Situ Preparation of 5-acylsulfanyl-histidine Followed by Hydrolysis and Oxidation (Compound 24)

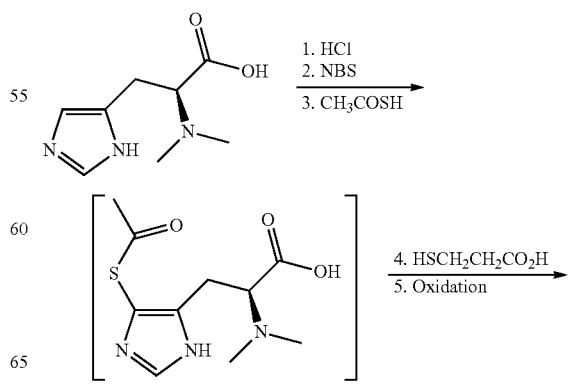

-continued

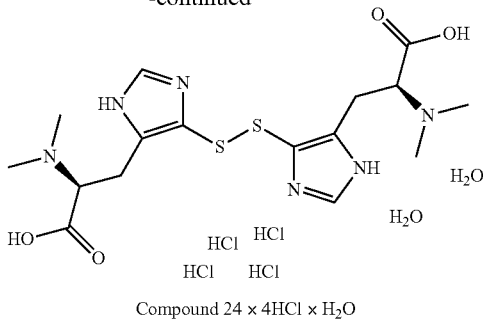

Compound 24 × 4HCl × H₂O

The hydrochloride of monohydrated α,N,N(dimethyl)-histidine (2.43 g; 10 mmoles; 1 eq.) is dissolved in 54 mL of demineralized water containing a 37% concentrated hydrochloric acid solution (835 µL; 985 mg; 10 mmoles; 1 eq.), then the solution is cooled to 1° C. Very strong stirring is maintained. N-Bromosuccinimide (2.31 g; 13 mmoles; 1.3 eq.). is added rapidly. After 2 minutes, thioacetic acid (3.0 mL; 3.14 g; 40 mmoles; 4 eq.) is added very rapidly. Vigorous stirring is maintained at 0° C. for 30 minutes. The slightly yellow solution obtained is extracted with 2 times 120 mL of ethyl acetate. After hot hydrolysis, oxidation and purification on DOWEX 50WX2-400 resin, the hydrated hydrochloride of the disulfide of L-5-sulfanyl-α,N,N(dimethyl)-histidine (Compound 24×4HCl×H₂O), 1.2 g, 41%) is obtained in the form of a beige powder.

¹H NMR (D₂O, 400 MHz): δ (ppm)=3.01 (s, 2×6H); 3.37 (dd, J=14.6 Hz, J=11.2 Hz, 2×1H); 3.51 (dd, J=14.6 Hz, J=4.0 Hz, 2×1H); 4.09 (dd, J=11.2 Hz, J=4.0 Hz, 2×1H); 8.86 (s, 2×1H).

LCMS (APCI): 429.2 [M+H]⁺ b) Preparation of the Compound 24 Free Base

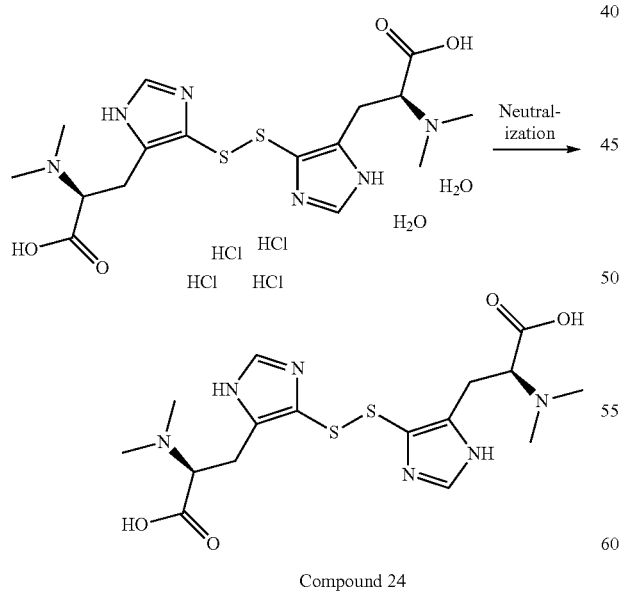

Compound 24

The hydrated hydrochloride of the disulfide of L-5-sulfanyl-α,N,N(dimethyl)-histidine (3.6 g; 5.89 mmoles; 1 eq.) is dissolved in 53 mL of demineralized water. The resin Amberlite® IRA-410 (8 g) in hydrogen carbonate form (according to K. A. Piez et al., J. Biol. Chem. 194, 669-672 (1952)) is added. The suspension is stirred under a vacuum for 30 minutes, then filtered. The filtrate is evaporated leading to the disulfide of L-5-sulfanyl-α,N,N(dimethyl)-histidine free base (Compound 24) (2.47 g, 84%) in the form of a yellow solid.

¹H NMR (D₂O, 400 MHz): δ (ppm)=2.88 (s, 2×6H); 2.92 (m, 2×2H); 3.70 (m, 2×1H); 8.17 (s, 2×1H).

c) Obtention of Compound 25 by Reduction of Compound 18×4HCl×H₂O)

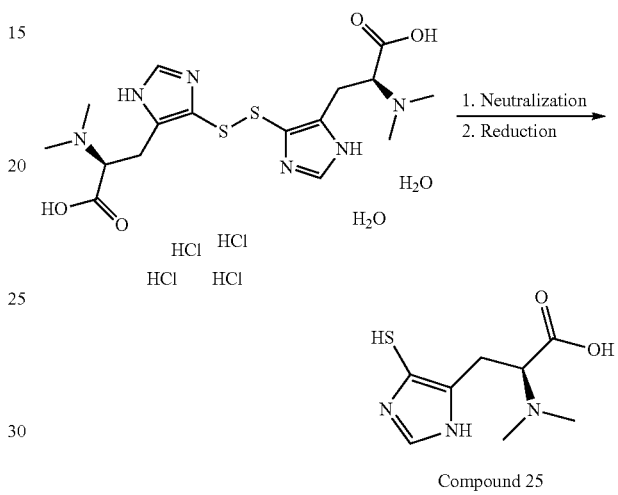

Compound 25

The hydrated hydrochloride of the disulfide of L-5-sulfanyl-α,N,N(dimethyl)-histidine (1.2 g; 2.07 mmoles; 0.5 eq.) is dissolved in 40 mL of demineralized water. The resin Amberlite® IRA-410 (2 g) in hydrogen carbonate form is added. The suspension is stirred under a vacuum for 30 minutes and then filtered. After reduction with dithiothreitol (967 mg; 6.20 mmoles; 1.5 eq.) and crystallization with absolute ethanol, under nitrogen, L-5-sulfanyl-α,N,N(dimethyl)-histidine (Compound 25) (450 mg, 58%) is obtained in the form of a white solid.

¹H NMR (D₂O, 400 MHz): δ (ppm)=3.00 (s, 6H); 3.23 (dd, J=15.5 Hz and J=7.5 Hz, 1H); 3.31 (dd, J=15.5 Hz and J=5.8 Hz, 1H); 4.00 (dd, J=7.5 Hz and J=5.8 Hz, 1H); 8.28 (s, 1H).

¹³C NMR (D₂O, 75 MHz): δ (ppm)=22.7; 41.8; 67.3; 124.5; 129.6; 131.7; 171.0.

LCMS (APCI): 216.1 [M+H]+ d) Analytical Monitoring of the Hydrolysis of the 5-acylsulfanyl Compound (Compound 2) into the 5-sulfanylhistidine Compound 25

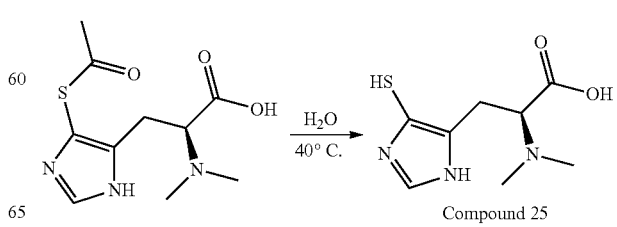

Compound 25

Compound 2 is prepared and purified by column as described in Example 3, using an ethyl acetate/ethanol gradient followed by elution with water. The aqueous fraction containing the pure compound 2 is placed in a water bath at 40° C. and heated under stirring for 8 h. Samples are collected every 60 minutes and the mixture is analyzed by HPLC.

The hydrolysis of compound 2 is nearly complete after 8 h, and compound 19 is obtained with a yield of 70%.

TABLE 2

Monitoring of the formation of compound 25 by hydrolysis of compound 2:

| | t (h) | | | | |
|---|---|---|---|---|---|
| | 0 | 1 | 2 | 3 | 5 | 8 |
| % compound 25 | 0% | 14% | 23% | 34% | 49% | 70% |

Example 28 a) "One Pot" Preparation of L-5-sulfanyl-α,N,N,N (trimethyl)-histidine Via In-Situ Preparation of 5-acylsulfanyl-histidine Followed by Hydrolysis (Compound 26)

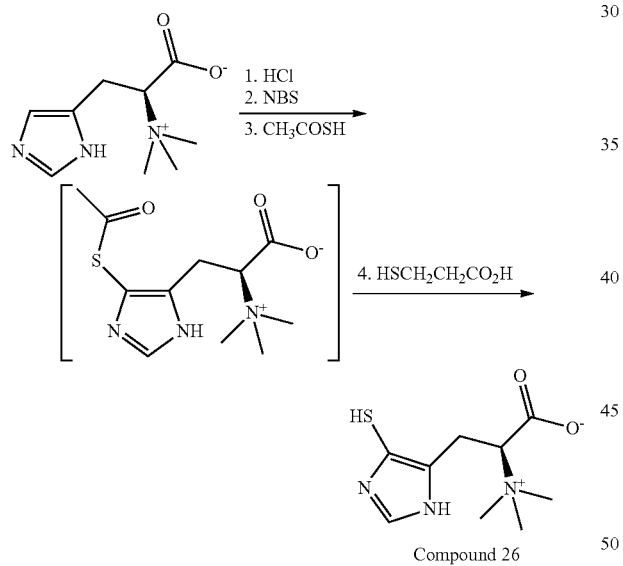

L-Hercynine (5.02 g; 25 mmoles; 1 eq.) is dissolved in 135 mL of demineralized water and a 37% concentrated hydrochloric acid solution (4.17 mL; 4.93 g; 50 mmoles; 2 eq.) is added; then the solution is cooled to 0° C. Under strong stirring, N-bromosuccinimide (5.78 g; 32.5 mmoles; 1.3 eq.) is added. After 5 minutes, thioacetic acid (18.33 mL; 19.61 g; 250 mmoles; 10 eq.) is added very rapidly. Stirring is maintained for 40 minutes. The solution is extracted with 2 times 135 mL of ethyl acetate. 3-Mercaptopropionic acid (11.07 ml: 13.4 g; 125 mmoles; 5 eq.) is added to the aqueous phase, then the solution is heated at 130° C. for 3 h. After extraction, neutralization and crystallization in the presence of dithiothreitol (1.95 g; 12.5 mmoles; 0.5 eq.), L-5-sulfanyl-α,N,N,N(trimethyl)-histidine (Compound 26) (2.22 g; 38%; 58% with respect to the quantity of the intermediate SAc) is obtained in the form of a white powder (to be stored under an inert atmosphere).

$^1$H NMR (D$_2$O, 400 MHz): δ (ppm)=3.29 (s, 9H); 3.19 (m, 1H); 3.35 (m, 1H); 4.00 (dd, J=10.6 Hz, J=3.9 Hz, 1H); 8.22 (s, 1H).

LCMS (APCI): 230.0 [M+H]+ b) Analytical Monitoring by $^1$H NMR of the Hydrolysis of the 5-acylsulfanyl Compound 3 into the Compound L-5-sulfanyl-α,N,N,N(trimethyl)-histidine (Compound 26) in the Presence of a Thiol

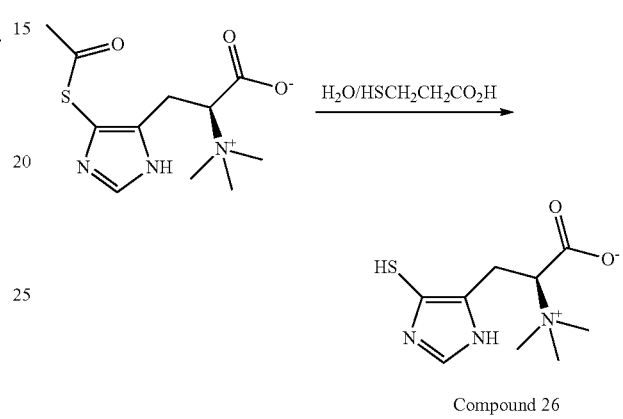

Compound 26

Compound 3 is prepared and purified by column as described in Example 5. 100 mg (0.33 mmoles, 1 eq.) of compound 3 are dissolved in 2.4 mL of D2O. 172 mg of 3-mercaptopropionic acid (142 µL, 5 equivalents) are added, and the solution is heated at 40° C. The conversion is monitored by $^1$H NMR and by HPLC-ELSD. The yield of hydrolysis of compound 3 is 90% after 3 h (monitored by $^1$H NMR). Compound 26 is formed after 3 h 30 with a yield of 97% (HPLC-ELSD).

c) Preparation of the Compound L-5-sulfanyl-α,N,N,N(trimethyl)-histidine (Compound 26) by Hydrolysis of the 5-acylsulfanyl Compound 3

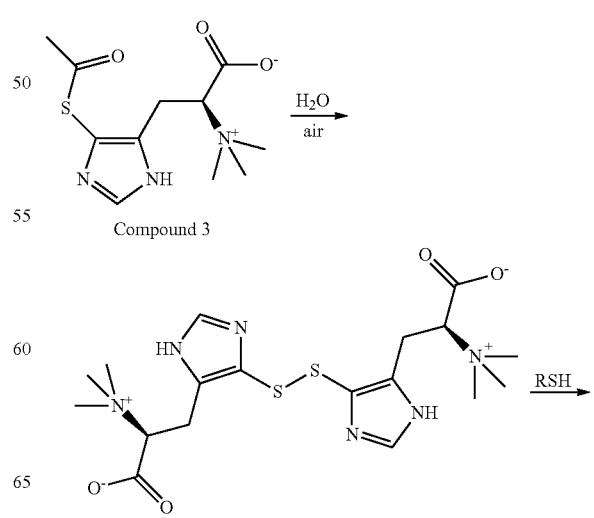

33

-continued

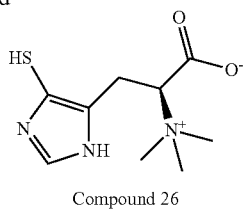

Compound 26

Compound 3 is prepared and purified by column as described in Example 5. 170 mg (0.6 mmoles) of compound 3 are dissolved in 10 mL of water, and the solution is heated at 90° C. in air for 7 h. The conversion is monitored by HPLC. The hydrolysis of compound 3 is complete after 7 h. The solution is evaporated to dryness. The residue is dissolved in a mixture of 5 mL of methanol and 93 mg (0.6 mmol) of dithiothreitol. After stirring for 4 h under an inert atmosphere, 2 mL of ethanol are added. A precipitate forms immediately, which is filtered and washed with ethanol (2×2 mL), then with ethyl ether (2×2 mL). After drying, 104 mg (72%) of L-5-sulfanyl-α,N,N,N(trimethyl)-histidine are obtained in the form of a beige powder.

The $^1$H NMR and mass spectra are identical to those obtained in Example 28a.

d) Preparation of the disulfide of L-5-sulfanyl-α,N,N,N(trimethyl)-histidine (Compound 27)

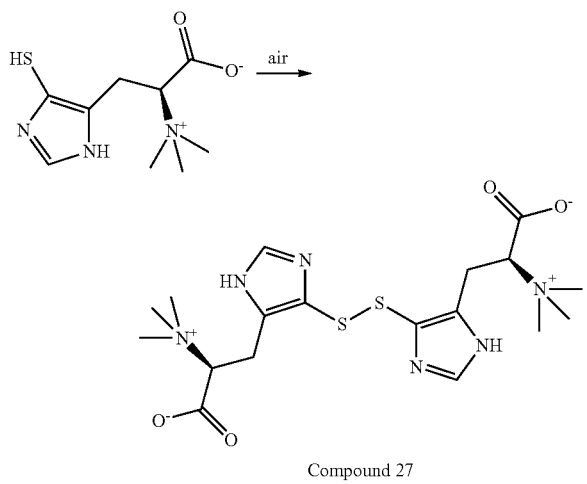

Compound 27

L-5-Sulfanyl-α,N,N,N(trimethyl)-histidine (Compound 26, 300 mg, 1.29 mmoles, 1 eq.) is dissolved in 50 mL of demineralized water. The colorless solution is stirred at ambient temperature for 4 days. After filtration and lyophilization of the filtrate, the disulfide of L-5-sulfanyl-α,N,N,N(trimethyl)-histidine (Compound 27) (263 mg; 89%) is obtained in the form of a yellow powder.

$^1$H NMR (D$_2$O, 400 MHz): δ (ppm)=2.68 (dd, J=13.5 Hz, J=11.0 Hz, 2×1H); 2.75 (dd, J=13.5 Hz, J=4.3 Hz, 2×1H); 3.19 (s, 2×9H); 3.68 (dd, J=11.0 Hz, J=4.3 Hz, 2×1H); 7.97 (s, 2×1H).

LCMS (APCI): 457.1 [M+H]+.

34 e) Analytical Monitoring by HPLC of the Hydrolysis of the 5-acylsulfanyl Compound 3 and Oxidation In Situ into Compound 27

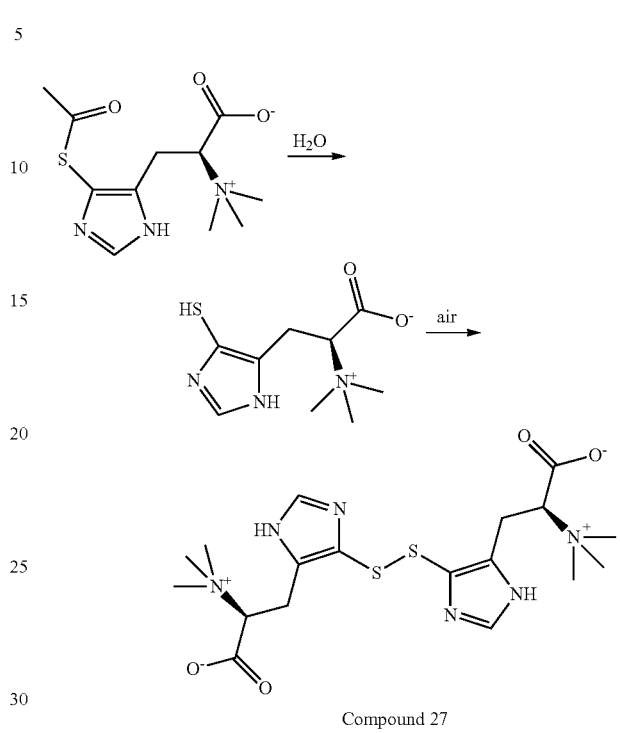

Compound 27

Compound 3 is prepared and purified by column as described in Example 5, using an ethyl acetate/ethanol gradient, followed by elution with water. The aqueous fraction containing the pure compound 3 is placed in a water bath at 40° C. and heated under stirring for two days. Samples are collected every hour, and the mixture is analyzed by HPLC.

The hydrolysis of compound 3 is nearly complete after 2 days, and compound 27 is obtained with a yield of 80%.

TABLE 3

| Monitoring of the hydrolysis of compound 3: | | | | | | | |
|---|---|---|---|---|---|---|---|
| | t | | | | | | |
| | 0 h | 2 h | 4 h | 6 h | 8 h | 18 h | 2 j |
| % hydrolysis | 0% | 7% | 21% | 38% | 60% | 85% | 95% | f) Analytical Monitoring by $^1$H NMR of the Hydrolysis of the 5-acylsulfanyl Compound 3 and Oxidation In Situ into Compound 27

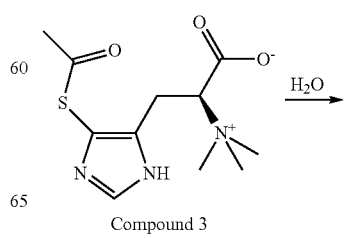

Compound 3

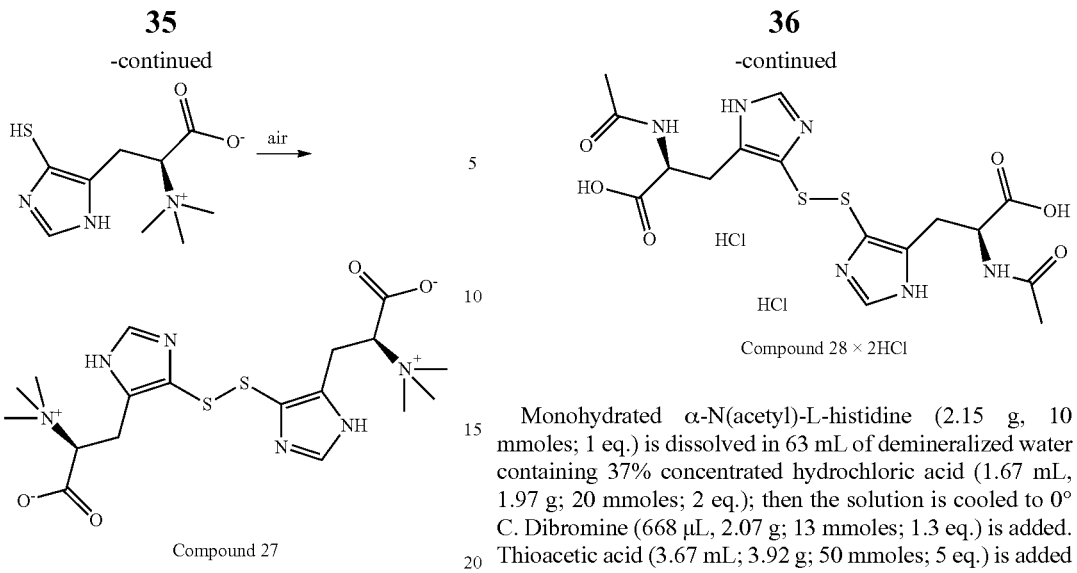

Compound 27

Compound 3 is prepared and purified by column as described in Example 5. 30 mg of compound 3 are dissolved in 600 μL of $D_2O$, the solution is transferred to an NMR tube, which is stored at ambient temperature. The conversion is monitored by $^1$H NMR. The hydrolysis of compound 3 is nearly complete after 2 days, and a mixture which contains the disulfide 27 and the thiol 26 (~3:1) is obtained.

TABLE 4

Monitoring of the hydrolysis of compound 3:

| | t | | | |
|---|---|---|---|---|
| | 0 h | 2 h | 10 h | 2 j |
| % hydrolysis | 0% | 19% | 26% | 86% |

Example 29 a) "One Pot" Preparation of the Disulfide of L-5-sulfanyl-α-N(acetyl)-histidine (Compound 28 Hydrochloride) Via In-Situ Preparation of 5-acyl-sulfanyl-histidine Followed by Hydrolysis and Oxidation

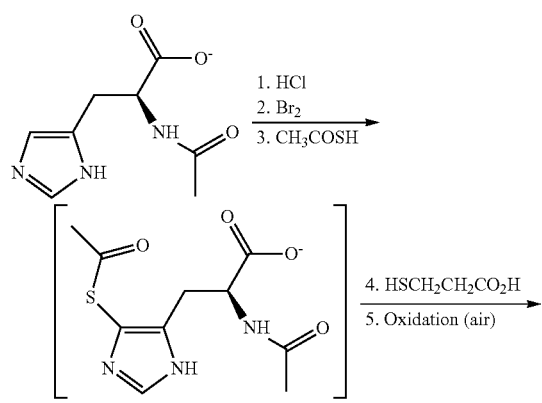

Compound 28 × 2HCl

Monohydrated α-N(acetyl)-L-histidine (2.15 g, 10 mmoles; 1 eq.) is dissolved in 63 mL of demineralized water containing 37% concentrated hydrochloric acid (1.67 mL, 1.97 g; 20 mmoles; 2 eq.); then the solution is cooled to 0° C. Dibromine (668 μL, 2.07 g; 13 mmoles; 1.3 eq.) is added. Thioacetic acid (3.67 mL; 3.92 g; 50 mmoles; 5 eq.) is added all at once. Stirring is maintained at 0° C. for 45 minutes. The solution is reheated at ambient temperature. 3-Mercaptopropionic acid (5.26 mL, 6.36 g; 60 mmoles; 6 eq.) is added, then the solution is heated at 80° C. overnight. The solution is cooled at ambient temperature, then extracted with 4 times 50 mL of ethyl acetate. The aqueous phase is purified on silica in order to obtain the hydrochloride of the disulfide of L-5-sulfanyl-α,N(acetyl)-histidine (compound 28) in the form of an orange oil (520 mg, 17%; 36% with respect to the quantity of the intermediate SAc).

$^1$H NMR ($D_2O$, 400 MHz): δ (ppm)=1.86 (s, 2×3H); 2.92 (dd, J=15.0 Hz, J=8.0 Hz, 2×1H); 3.03 (dd, J=15.0 Hz, J=5.5 Hz, 2×1H); 4.47 (dd, J=8.0 Hz, J=5.5 Hz, 2×1H); 8.73 (s, 2×1H).

LCMS (APCI): 457.4 [M+H]+ b) Preparation of L-5-sulfanyl-α,N(acetyl)-histidine (Compound 29)

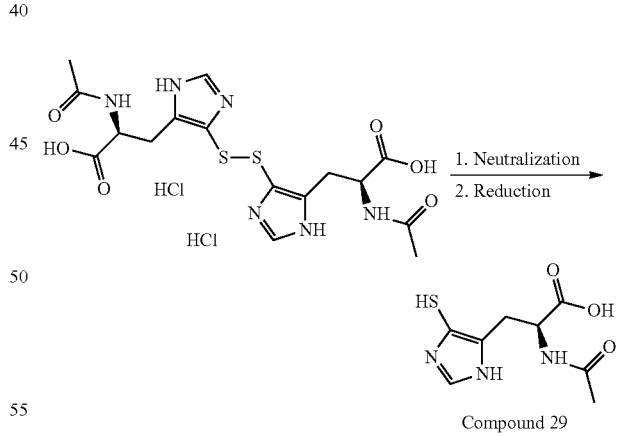

Compound 29

The hydrochloride of the disulfide of L-5-sulfanyl-α,N (acetyl)-histidine (Compound 28) (520 mg; 834 μmoles, 1 eq.) is dissolved in 50 mL of water, then the pH of the brown colored solution is adjusted to 4.5 by adding $NH_4OH$. 3-Mercaptopropionic acid (4.38 mL; 5.31 g; 50 mmoles; 5 eq.) is added. The solution is heated at 70° C. for 2 h. The solution is extracted with 4 times 50 mL of ethyl acetate. The aqueous phase is evaporated to dryness yielding L-5-sulfanyl-α,N(acetyl)-histidine (Compound 29) (390 mg; 86%) in the form of a beige solid.

¹H NMR (D₂O, 400 MHz): δ (ppm)=1.97 (s, 3H); 3.01 (dd, J=15.2 Hz, J=8.6 Hz, 1H); 3.16 (dd, J=15.2 Hz, J=4.8 Hz, 1H); 4.50 (dd, J=8.6 Hz, J=4.8 Hz, 1H); 8.22 (s, 1H).

LCMS (APCI): 230.0 [M+H]⁺

Example 30: "One Pot" Preparation of L-5-sulfanylcarnosine Via In-Situ Preparation of 5-acylsulfanyl-histidine Followed by Hydrolysis (Compound 30)

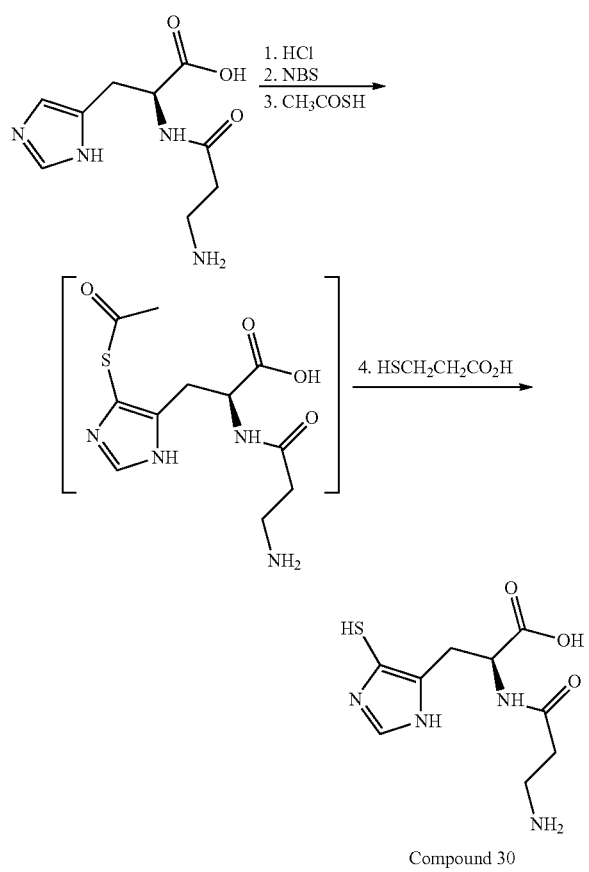

Compound 30

L-Carnosine (425 mg; 1.88 mmoles; 1 eq.) is dissolved in 12 mL of demineralized water containing a 37% concentrated hydrochloric acid solution (370 mg; 3.75 mmoles; 2 eq.), then the solution is cooled to 0° C. N-Bromosuccinimide (440 mg; 2.44 mmoles; 1.3 eq.) is added in one portion: the solution turns limpid orange. Thioacetic acid (960 µL; 1.03 g, 13.14 mmoles; 7 eq.) is added. The mixture is stirred at 0° C. for 1 h. The solution is extracted with 4 times 12 mL of ethyl acetate. After neutralization and purification on silica in the presence of dithiothreitol (290 mg; 1.88 mmoles; 1 eq.), L-5-sulfanylcarnosine (Compound 30) (70 mg; 14%; 22% with respect to the quantity of the intermediate SAc) is obtained in the form of a colorless lacquer.

¹H NMR (D₂O, 400 MHz): δ (ppm)=2.69 (t, J=6.7 Hz, 2H); 3.00 (m, 1H); 3.12 (m, 1H); 3.23 (t, J=6.7 Hz, 2H); 4.43 (dd, J=8.5 Hz, J=4.2 Hz, 1H); 8.20 (s, 1H).

LCMS (APCI): 259.1 [M+H]+

Example 31: Preparation of Compounds 31 and 32 a) "One Pot" Preparation of the Disulfide of iso-ovothiol A Via In-Situ Preparation of 5-acetylsulfanyl-1-methylhistidine Followed by Hydrolysis and Oxidation (Compound 31)

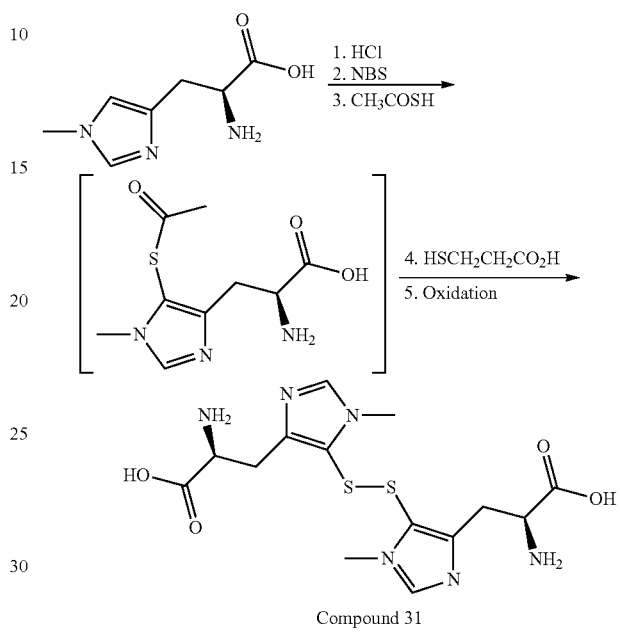

Compound 31

1-Methyl-L-histidine (0.84 g; 5 mmoles; 1 eq.) is dissolved in 35 mL of demineralized water, and a 37% concentrated hydrochloric acid solution (835 µL (10 mmoles; 2 eq.) is added; then the solution is cooled to 1° C. Very strong stirring is maintained. N-Bromosuccinimide (1.17 g; 6.5 mmoles; 1.3 eq.) is added rapidly. After 3 minutes, thioacetic acid (2.57 mL; 2.74 g; 35 mmoles; 7 eq.) is added very rapidly. Vigorous stirring is maintained at 0° C. for 30 minutes. The solution is extracted with 40 mL of ethyl acetate, then 3-mercaptopropionic acid (2.2 mL; 2.65 g; 25 mmoles; 5 eq.) is added to the aqueous phase. The hydrolysis is carried out by heating at 100° C. for 20 h. After cooling of the solution, the reaction medium is extracted with 4 times 35 mL of ethyl acetate. After oxidation and purification with DOWEX 50WX2-400 resin, the disulfide of L-1-methyl-L-5-sulfanylhistidine (Compound 31) (740 mg, 65%, 90% with respect to the quantity of the intermediate SAc) is obtained in the form of a brown powder.

¹H NMR (D₂O+DCl, 400 MHz): δ (ppm)=3.14 (m, 2×2H); 3.85 (s, 2×3H); 4.17 (m, 2×1H); 8.89 (s, 2×1H).

LCMS (APCI): 401.1 [M+H]+ b) Preparation of iso-ovothiol A (Compound 32)

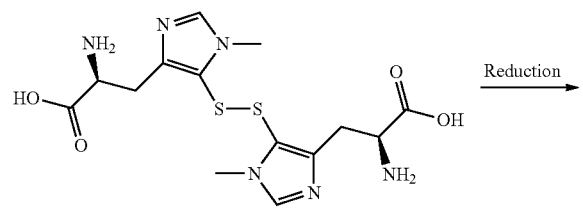

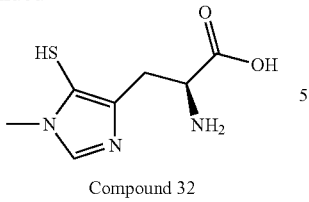

Compound 32

The disulfide of L-5-sulfanyl-1-methylhistidine (Compound 25) (427 mg; 0.52 mmoles, 1 eq.) is suspended in 25 mL of methanol. The mixture is heated to 50° C., then dithiothreitol (299 mg; 1.92 mmoles; 2 eq.) is added. After stirring for 1 h at ambient temperature and precipitation with ethyl ether, L-5-sulfanyl-1-methylhistidine (iso-ovothiol A, Compound 32) (295 mg; 69%) is obtained in the form of a slightly grayish powder.

$^1$H NMR (D$_2$O, 400 MHz): δ (ppm)=3.19 (dd, J=15.7 Hz, J=7.2 Hz, 1H); 3.29 (dd, J=15.7 Hz, J=5.2 Hz, 1H); 3.66 (s, 3H); 4.09 (dd, J=7.1 Hz, J=5.2 Hz, 1H); 8.33 (s, 1H).

LCMS (APCI): 202.1 [M+H]+

Example 32: Preparation of the Disulfide of L-5-sulfanyl-α,N,N(dimethyl)-1-methylhistidine Via Hydrolysis of the 5-acetylsulfanyl-α,N,N(dimethyl)-1-methylhistidine Derivative Followed by Air Oxidation (Compound 33)

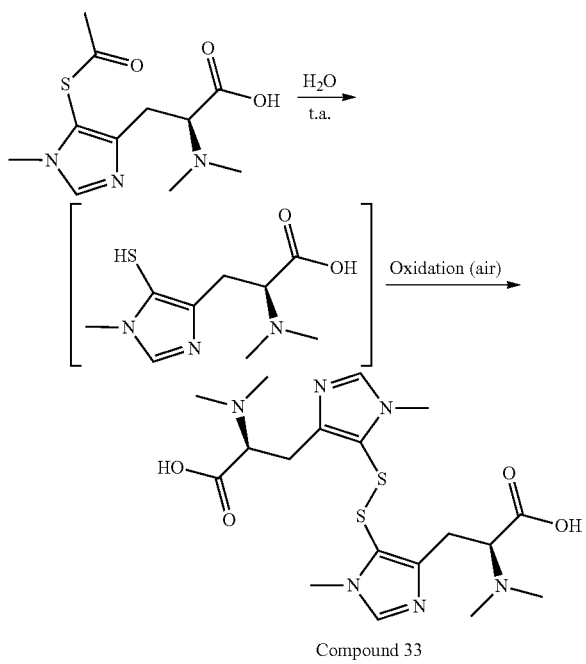

Compound 33

Compound 5 is prepared and purified by column as described in Example 8. 180 mg (0.63 mmoles, 1 eq.) of compound 5 are dissolved in 20 mL of water. The limpid solution is stirred in the presence of oxygen for 20 h at ambient temperature. After lyophilization, the disulfide of L-5-sulfanyl-α,N,N(dimethyl)-1-methylhistidine (Compound 33, 98%) is obtained in the form of a greenish amorphous solid.

$^1$H NMR (D$_2$O, 400 MHz): δ (ppm)=2.97 (s, 2×6H); 3.17 (m, 2×1H); 3.28 (dd, J=15.8 Hz and J=4.3 Hz, 2×1H); 3.69 (s, 2×3H); 4.00 (m, 2×1H); 8.44 (s, 2×1H).

LCMS (APCI): 457.2 [M+H]+

Example 33: "One Pot" Preparation of the Disulfide of L-5-sulfanyl-α,N,N,N(trimethyl)-1-methylhistidine (Compound 34 Dihydrochloride) Via In-Situ Preparation of L-5-acetylsulfanyl-α,N,N,N(trimethyl)-1-methylhistidine Followed by Hydrolysis and Oxidation

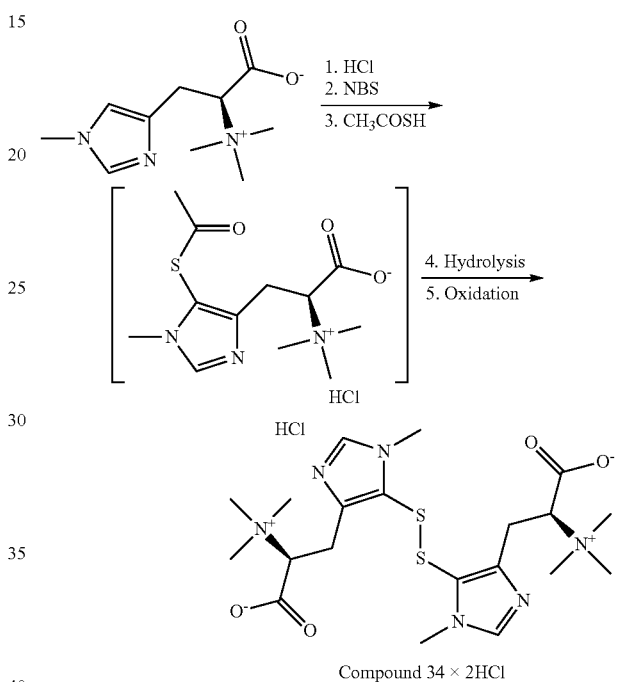

Compound 34 × 2HCl

1-Methyl-hercynine (510 mg, 2 mmoles; 1 eq.) is dissolved in 15 mL of demineralized water containing a 37% concentrated hydrochloric acid solution (170 μL, 2 mmoles; 1 eq.), then the solution is cooled to 0° C. Very strong stirring is maintained. N-Bromosuccinimide (465 mg, 2.6 mmoles; 1.3 eq.) is added rapidly. After 3 minutes, thioacetic acid (740 μL, 10 mmoles; 5 eq.) is added very rapidly. Vigorous stirring is maintained at 0° C. for 30 minutes. The mixture is extracted with 2×20 mL of ethyl acetate, then diluted in 160 mL of an ethyl acetate/ethanol mixture (3/1) for purification on a silica column (ethyl acetate/ethanol/water 2/2/1). The slightly pink oil obtained is oxidized with dimethyl sulfoxide (140 μL, 2 moles, 1 eq.) in a solution of glacial acetic acid. The solution is heated for one hour at 80° C. The dihydrochloride of the disulfide of L-5-sulfanyl-α,N,N,N(trimethyl)-1-methylhistidine (compound 34) is obtained after purification on a silica column (ethyl acetate/ethanol/water 2/2/1, followed by elution with 0.5M hydrochloric acid) in the form of a slightly yellow oil (110 mg, 10%).

$^1$H NMR (D$_2$O, 400 MHz): δ (ppm)=3.30 (s, 2×9H); 3.61 (dd, J=14.1 Hz and 3.4 Hz, 2×1H); 3.72 (m, 2×1H); 3.73 (s, 2×3H); 4.09 (dd, J=12.2 Hz and 3.4 Hz, 2×1H); 8.98 (s, 2×1H).

LCMS (APCI): 485.1 [M+H]+

Example 34: Preparation of the L-5-sulfanyl-α,N(L-alanyl)-histidine Derivative (Compound 35) by Hydrolysis of the 5-acylsulfanyl Compound

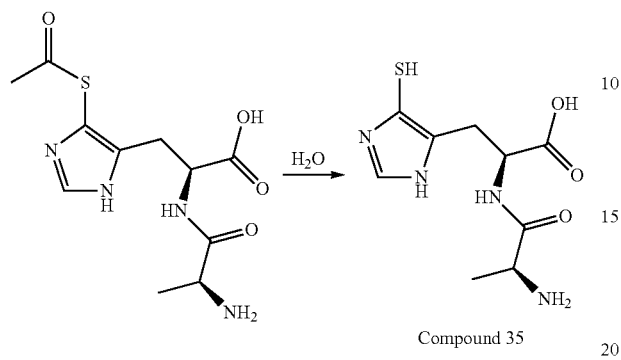

Compound 35

Compound 7 is prepared and purified by column as described in Example 10. 340 mg (1 mmole, 1 eq.) of compound 7 are dissolved in 20 mL of water. The limpid solution is stirred with protection from oxygen for 6 days at ambient temperature. After evaporation to dryness, L-5-sulfanyl-α,N(L-alanyl)-histidine (Compound 35, 92%) is obtained in the form of a beige amorphous solid.

$^1$H NMR (D$_2$O, 400 MHz): δ (ppm)=1.42 (d, J=7.2 Hz, 3H); 3.12 (dd, J=15.2 and J=8.0 Hz, 1H); 3.22 (dd, J=15.2 Hz and J=6.2 Hz, 1H); 4.05 (q, J=7.2 Hz, 1H); 4.65 (m, 1H); 8.71 (s, 1H).

LCMS (APCI): 258.9 [M+H]+

Example 35: Preparation of the Disulfide of 5-sulfanyl-α,N(pentanoyl)-histidine (Compound 36) by Hydrolysis and Oxidation of the Compound 5-acetylsulfanyl-α,N(pentanoyl)-histidine

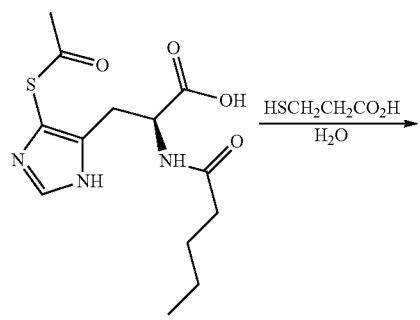

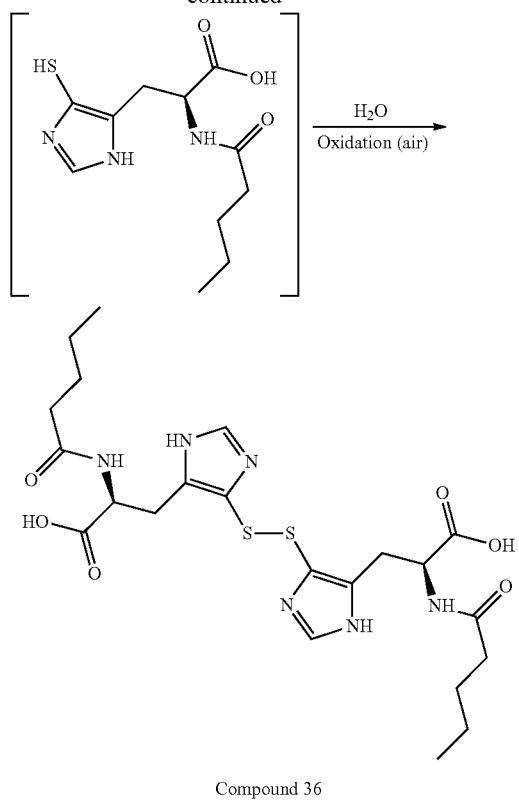

Compound 36

The 5-acetylsulfanyl-α,N(pentanoyl)-histidine derivative (compound 8) is prepared and purified as described in Example 11. 320 mg (0.9 mmole; 1 eq.) of compound 8 are dissolved in 8.0 mL of demineralized water. 3-Mercaptopropionic acid (400 µL, 4.60 mmoles; 5 eq.) is added. The solution is heated at 90° C. for 3 h. The reaction mixture is extracted with 4×10 mL of ethyl acetate, then the aqueous phase is evaporated to dryness. The residue is dissolved in 10 mL of water. The solution is heated at 90° C. under stirring for 2 hours, then at ambient temperature for 18 hours. After evaporation to dryness, the disulfide of L-5-sulfanyl-α,N(pentanoyl)-histidine (Compound 36) is obtained in the form of an orange lacquer (44%).

LCMS (APCI): 541.2 [M+H]+

TABLE 5

Summary of the examples:

| Example | Compound prepared | Structure |
|---|---|---|
| 1<br>2 | 1<br>1 | 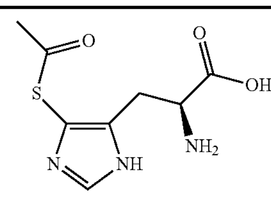 |

TABLE 5-continued

Summary of the examples:

| Example | Compound prepared | Structure |
|---|---|---|
| 3<br>4 | 2<br>2 | (structure: S-acetyl imidazole with L-alanine N,N-dimethylamino carboxylic acid) |
| 5<br>6 | 3<br>3 | (structure: S-acetyl imidazole with L-alanine trimethylammonium carboxylate) |
| 7 | 4 | (structure: S-acetyl imidazole with L-histidine-glycinamide) |
| 8 | 5 | (structure: S-acetyl N-methylimidazole with L-alanine N,N-dimethylamino carboxylic acid) |
| 9 | 6 | (structure: S-acetyl N-methylimidazole with L-alanine trimethylammonium carboxylate) |
| 10 | 7 | (structure: S-acetyl imidazole with L-histidine-alaninamide) |

TABLE 5-continued

Summary of the examples:

| Example | Compound prepared | Structure |
|---|---|---|
| 11 | 8 | 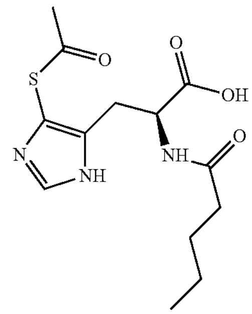 [SMILES: CCCCC(=O)N[C@@H](Cc1[nH]cnc1SC(C)=O)C(=O)O] |
| 12 | 9 | 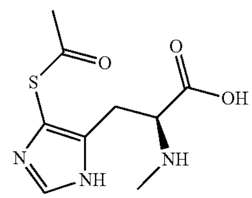 [SMILES: CN[C@@H](Cc1[nH]cnc1SC(C)=O)C(=O)O] |
| 13 | 10 | 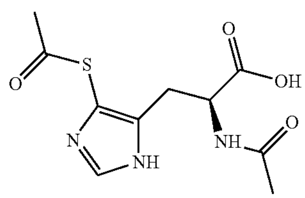 [SMILES: CC(=O)N[C@@H](Cc1[nH]cnc1SC(C)=O)C(=O)O] |
| 14 | 11 | 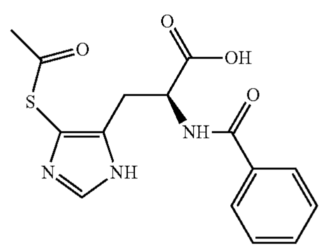 [SMILES: CC(=O)Sc1nc[nH]c1C[C@H](NC(=O)c1ccccc1)C(=O)O] |
| 15 | 12 | 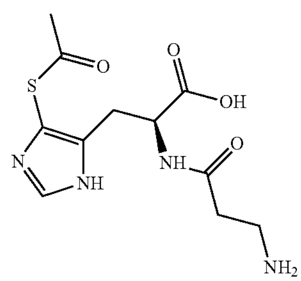 [SMILES: CC(=O)Sc1nc[nH]c1C[C@H](NC(=O)CCN)C(=O)O] |
| 16 17 | 13 13 | |

TABLE 5-continued

Summary of the examples:

| Example | Compound prepared | Structure |
|---|---|---|
| 18 | 14 | (benzoyl-S-imidazole-L-alanine with COOH, NH2) |
| 19 | 15 | (benzoyl-S-imidazole-L-alanine with N,N-dimethylamino, COOH) |
| 20 | 16 | (benzoyl-S-imidazole-alanine with trimethylammonium, carboxylate) |
| 21 | 17 | (acetyl-S-imidazole-alanine-phenylalanine dipeptide) |
| 22 | 18 | (HS-imidazole-L-alanine with COOH, NH2) |
| 23 | 19 | (HS-imidazole-D-alanine with COOH, NH2) |
| 24 | 20 | (HS-imidazole-alanine racemic with COOH, NH2) |

TABLE 5-continued

Summary of the examples:

| Example | Compound prepared | Structure |
|---|---|---|
| 25 | 21 × 4HCl × 2H2O | (structure shown) 4HCl 2H₂O |
| 26a | 22 | (structure shown) |
| 26b | 23 | (structure shown) |
| 27a | 24 × 4HCl × 2H2O | (structure shown) HCl HCl HCl HCl H₂O H₂O |
| 27b | 24 | (structure shown) |
| 27c | 25 | (structure shown) |
| 27d | 25 | |

TABLE 5-continued

Summary of the examples:

| Example | Compound prepared | Structure |
|---|---|---|
| 28a<br>28b<br>28c | 26<br>26<br>26 | (structure: mercapto-imidazole with trimethylammonium carboxylate) |
| 28d<br>28e<br>28f | 27<br>27<br>27 | (structure: disulfide-linked bis-imidazole with two trimethylammonium carboxylate groups) |
| 29a | 28 × 2HCl | (structure: disulfide-linked bis(N-acetyl-histidine), 2 HCl) |
| 29b | 29 | (structure: 2-mercapto-N-acetyl-histidine) |
| 30 | 30 | (structure: 2-mercapto-histidine with β-alanyl amide) |
| 31a | 31 | (structure: disulfide-linked bis(N-methyl-imidazole histidine)) |

TABLE 5-continued

Summary of the examples:

| Example | Compound prepared | Structure |
|---|---|---|
| 31b | 32 | (structure) |
| 32 | 33 | (structure) |
| 33 | 34 × 2HCl | (structure) |
| 34 | 35 | (structure) |
| 35 | 36 | (structure) |

The invention claimed is:
1. 5-acylsulfanyl-histidine compound of formula (I):

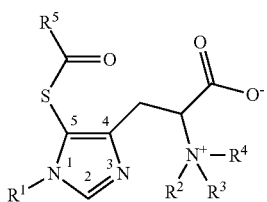

where:
$R^1$=H or alkyl;
$R^2$=$R^3$=H or alkyl;
$R^4$=H, alkyl, alkyl (C=O), substituted alkyl (C=O), aryl (C=O), β-alanyl ($H_2NCH_2CH_2$ (C=O)), or α-amino-acyl;
$R^5$=alkyl or phenyl;
as well as all the stereoisomers, diastereoisomers and enantiomers, in particular in terms of the carbon atom bearing the COOH group, taken separately or in a mixture; and all the salts of pharmaceutically acceptable acids of said compound of formula (I).

2. The compound according to claim 1, wherein $R^4$ represents hydrogen, $CH_3$, acetyl, benzoyl, or β-alanyl ($H_2NCH_2CH_2$(C=O)) group.

3. The compound according to claim 1, wherein it is selected from the group consisting of:
L-5-acetylsulfanyl-histidine (Compound 1); and
L-5-acetylsulfanyl-histidine-α,N,N(dimethyl)-histidine (Compound 2);
L-5-acetylsulfanyl-α,N,N,N(trimethyl)-histidine (Compound 3);
L-5-acetylsulfanyl-α,N(glycinyl)-histidine (Compound 4);
L-5-acetylsulfanyl-α,N,N(dimethyl)-1-methylhistidine (Compound 5);
L-5-acetylsulfanyl-α,N,N,N(trimethyl)-1-methylhistidine (Compound 6);
L-5-acetylsulfanyl-α,N(alanyl)-histidine (Compound 7);
L-5-acetylsulfanyl-α,N(pentanoyl)-histidine (Compound 8);
L-5-acetylsulfanyl-α,N(methyl)-histidine (Compound 9);
L-5-acetylsulfanyl-α,N(acetyl)-histidine (Compound 10);
L-5-acetylsulfanyl-α,N(benzoyl)-histidine (Compound 11);
L-5-acetylsulfanyl-α,N(β-alanyl)-histidine (Compound 12);
L-1-methyl-5-acetylsulfanyl-histidine (Compound 13);
L-5-benzoylsulfanyl-histidine (Compound 14);
L-5-benzoylsulfanyl-α,N,N(dimethyl)-histidine (Compound 15);
L-5-benzoylsulfanyl-α,N,N,N(trimethyl)-histidine (Compound 16);
L-5-acetylsulfanyl-α,N(phenylalanyl)-histidine (Compound 17).

4. The compound according to claim 1, wherein the pharmaceutically acceptable acid is selected from a mineral acid such as hydrochloric, hydrobromic, hydroiodic, sulfuric, tartaric, phosphoric acid, or from an organic acid such as formic, acetic, trifluoroacetic, propionic, benzoic, maleic, fumaric, succinic, citric, oxalic, glyoxylic, aspartic acid; an alkanesulfonic acid such as a methanesulfonic, trifluoromethanesulfonic, ethanesulfonic acid and an arylsulfonic acid such as benzene- and paratoluenesulfonic acids.

5. Method (A) for preparing 5-acylsulfanyl-histidine compounds of formula (I), according to claim 1, wherein the preparation includes the following steps:
1) The reaction of histidine, racemic (DL) or one of the enantiomers thereof (D or L), or
a derivative of histidine which has been alkylated on the nitrogen in position 1 of the imidazole ring, racemic (DL) or one of the enantiomers thereof (D or L), or
a derivative of histidine which has been alkylated or acylated on the nitrogen of the α-amine function, racemic (DL) or one of the enantiomers thereof (D or L), or
a derivative of histidine which has been alkylated on the nitrogen in position 1 of the imidazole ring and alkylated or acylated on the nitrogen of the α-amine function, racemic (DL) or one of the enantiomers thereof (D or L),
in the presence of 1 to 2 equivalents of mineral or organic acid, with
a) an agent generating halogenium ions $X^+$ in a polar protic solvent, at temperatures of 0-25° C., then with
b) a sulfur-containing reagent of the carbothioic acid type of formula alkyl C(=O)SH or one of the salts thereof in a polar protic solvent,
then,
2) optionally, the purification by column liquid chromatography or any other purification method well known to the person skilled in the art.

6. The method according to claim 5, wherein the agent generating halogenium ions $X^+$ is selected from:
bromine $Br_2$, as commercial reagent or prepared in situ; or
NBS or any N-bromo-imide and N-bromo-amide derivative.

7. The method according to claim 5, wherein the polar protic solvent is water or an aqueous solution.

8. The method according to claim 5, wherein the sulfur-containing reagent of the carbothioic acid type is selected from thioacetic acid, thiobenzoic acid, potassium thioacetate, or mixtures thereof.

9. The method according to claim 5, wherein the temperature is 0-5° C.

10. Method (B) for preparing 5-sulfanylhistidine compounds of formula (II),

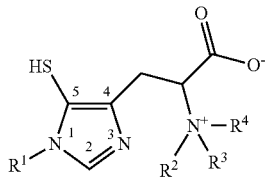

obtained from the 5-acylsulfanyl-histidine compounds of formula (I) described in method A A according to claim 5, wherein the preparation includes the following steps:
1) either directly (method B1):
e) by hydrolysis of the 5-acylsulfanyl-histidine compounds of formula (I) in a polar protic solvent by stirring at a temperature above 20° C. in the presence of a thiol,
f) then, optionally, purification by column liquid chromatography or any other purification method well known to the person skilled in the art, 2) or indirectly (method B2):
  f) by hydrolysis of the 5-acylsulfanyl-histidine compounds of formula (I) in a polar protic solvent by stirring at a temperature above 20° C. in order to obtain the corresponding disulfide,
  g) then reduction of the disulfide by reaction with a thiol,
  h) then, optionally, purification by column liquid chromatography or any other purification method well known to the person skilled in the art.

11. The method according to claim 10, wherein the polar protic solvent is selected from water or an aqueous solution.

12. The method according to claim 10, wherein the thiol is selected from mercaptopropionic acid, dithiothreitol or mixtures thereof.

13. The method according to claim 10, wherein the temperature is between 20 and 130° C.

14. Method (C) for preparing disulfides of the 5-sulfanyl-histidines in claim 10, wherein said disulfides are prepared:
  i) either directly from the 5-acylsulfanyl-histidine compounds of formula (I), characterized in that the preparation includes the following steps:
    a) hydrolysis of the 5-acylsulfanyl-histidine compounds of formula (I) in a polar protic solvent by air stirring and at a temperature above 20° C. in order to obtain the corresponding disulfide,
    b) then, optionally, purification by column liquid chromatography or any other purification method well known to the person skilled in the art;
  ii) or from 5-acylsulfanyl-histidines of formula (II), characterized in that the preparation includes the following steps:
    c) oxidation of the 5-sulfanylhistidine compounds of formula (II) by oxygen or dimethyl sulfoxide or any other oxidation method well known to the person skilled in the art,
    d) then, optionally, purification by column liquid chromatography or any other purification method well known to the person skilled in the art.

* * * * *